(12) United States Patent
Sekine et al.

(10) Patent No.: US 7,341,554 B2
(45) Date of Patent: Mar. 11, 2008

(54) ENDOSCOPIC TREATMENT SYSTEM

(75) Inventors: Ryuta Sekine, Koganei (JP); Raifu Matsui, Hino (JP); Yuta Okada, Hachioji (JP)

(73) Assignee: Olympus Corporation, Tokyo (JP)

( * ) Notice: Subject to any disclaimer, the term of this patent is extended or adjusted under 35 U.S.C. 154(b) by 131 days.

(21) Appl. No.: 10/635,044

(22) Filed: Aug. 5, 2003

(65) Prior Publication Data

US 2005/0119524 A1 Jun. 2, 2005

(30) Foreign Application Priority Data

Aug. 7, 2002 (JP) ............... 2002-230464

(51) Int. Cl.
*A61B 1/00* (2006.01)
*A61B 1/04* (2006.01)

(52) U.S. Cl. ..................... 600/106; 600/114

(58) Field of Classification Search ........ 600/104–107, 600/127, 129, 153, 114
See application file for complete search history.

(56) References Cited

U.S. PATENT DOCUMENTS 6,119,913 A 9/2000 Adams et al.

FOREIGN PATENT DOCUMENTS

| JP | 03-162845 | 7/1991 |
|---|---|---|
| JP | 2000-37347 | 2/2000 |
| WO | WO 96/18344 | 6/1996 |
| WO | WO 00/69344 | 11/2000 |

*Primary Examiner*—John P. Leubecker
*Assistant Examiner*—Philip R Smith
(74) *Attorney, Agent, or Firm*—Scully, Scott, Murphy & Presser, P.C.

(57) ABSTRACT

An endoscopic treatment system is designed to suture or resect a lesion while ensuring the ease of insertion into a deep region in the large intestine. The endoscopic treatment system comprises an endoscope and a therapeutic instruments insertion aid into which the endoscope is inserted. The endoscopic treatment system further comprises: a pair of clamp forceps that clamps and lifts a living-body tissue; a lateral hole formed in the therapeutic instruments insertion aid and used to control the position of the living-body tissue clamped and lifted by the pair of clamp forceps or to control the lifting thereof; a ligature used to ligate the living-body tissue whose position or lifting is controlled by the lateral hole; and a cutter used to resect the living-body tissue at a position between a region ligated with the ligature and a region clamped and lifted with the pair of clamp forceps.

27 Claims, 30 Drawing Sheets

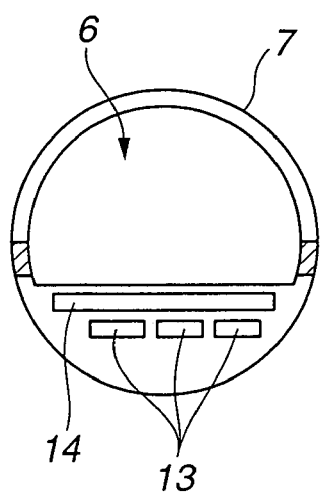
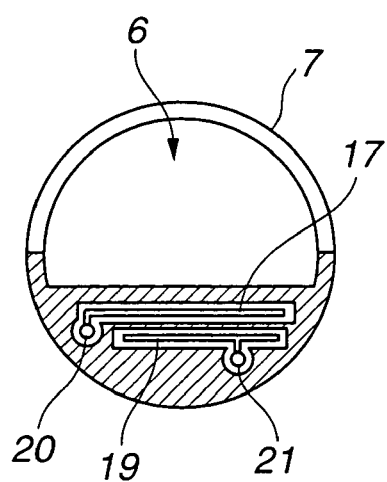
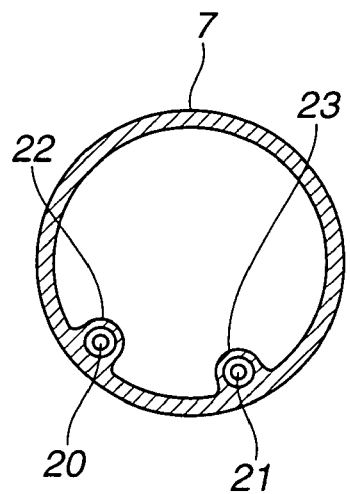
FIG.4 FIG.5 FIG.6
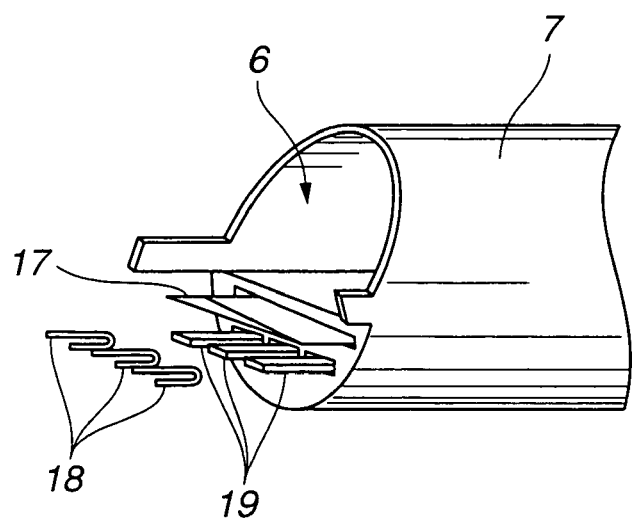
FIG.7

ENDOSCOPIC TREATMENT SYSTEM

This application claims the benefit of Japanese Application No. 2002-230464 filed on Aug. 7, 2002, the contents of which are incorporated by reference.

BACKGROUND OF THE INVENTION

1. Field of the Invention

The present invention relates to an endoscopic treatment system, or more specifically, to an endoscopic treatment system which treats a living-body tissue using an endoscope and a treatment instrument passed through a therapeutic instruments insertion aid, which is introduced into an intracavitary region.

2. Description of the Related Art

In the past, endoscopic mucosal resection in which an endoscope inserted into a body cavity through the mouth or anus is used to resect a mucosal lining affected by cancer has been widely adopted for the purpose of curing a carcinoma in the alimentary canal or the like without laparotomy.

In recent years, simultaneous resection of all layers including a mucosal lining and a muscular layer has been attempted in efforts to reliably resect a cancerous tissue and simplify histopathological diagnosis of a resected lesion.

However, there is technological difficulty in resecting all layers of an alimentary organ by utilizing a conventional endoscope. In particular, there is difficulty in suturing an alimentary organ in such a manner that the lumen of the alimentary organ and the abdominal cavity will not communicate with each other before or after resection of an intended region in a living-body tissue.

A suture and resection device used in combination with an endoscope to resect a lesion in an alimentary organ has been disclosed in, for example, PCT Japanese Translation Patent Publication No. 11-506943, U.S. Pat. No. 6,119,913, and Japanese Unexamined Patent Application Publication No. 2000-37347.

The PCT Japanese Translation Patent Publication No. 11-506943 proposes a surgical device having a mechanism, which is used to staple a luminal organ or resect a lesion, incorporated in the distal part of the surgical device. The surgical device has a channel through which an endoscope is passed, and a luminal organ is sutured or resected under a field of view offered by the passed-through endoscope.

Moreover, the U.S. Pat. No. 6,119,913 has proposed an endoscopic stapler freely detachably attached to an endoscope and used to suture or resect a living-body tissue.

The Japanese Unexamined Patent Application Publication No. 2000-37347 has proposed a treatment system that is a combination of a substantially hard insertion aid means, an endoscope, and a hard treatment instrument, and that is used to suture or resect the large intestine, or more specifically, the descending colon. The suture or resection is achieved while a tissue in the large intestine clamped and lifted using a pair of clamp forceps passed through the endoscope.

However, as proposed in the PCT Japanese Translation Patent Publication No. 11-506943 and the U.S. Pat. No. 6,119,913, a device for suturing or resecting a lesion under a field of view offered by an endoscope is designed to resect or suture a tissue to be resected by leading the tissue into an internal space of the suture and resection device. This poses a problem in that the size of a tissue capable of being resected is limited by the shape of the suture and resection system.

Moreover, as far as the devices and system proposed in the above publications are concerned, an endoscope is disposed more near to an operator than a suture and resection device is. Therefore, when the internal space of the suture and resection device is filled with a tissue led in, the field of view offered by the endoscope is blocked with the tissue. It becomes hard to identify a position to be sutured, a region to be resected, or a lesion.

Furthermore, the suture and resection devices proposed in the PCT Japanese Translation Patent Publication No. 11-506943, the U.S. Pat. No. 6,119,913, and the Japanese Unexamined Patent Application Publication No. 2000-37347 respectively are relatively large in size. No consideration is taken into the maneuverability in inserting the suture and resection device into a body cavity together with an endoscope. There is therefore difficulty in inserting the suture and resection device into a deep region in a relatively elongated tortuous luminal organ such as the large intestine.

SUMMARY OF THE INVENTION

An object of the present invention is to provide an endoscopic treatment system capable of reliably suturing or resecting an intended lesion while ensuring the ease of insertion into a deep region in the large intestine.

Briefly, the first aspect of the present invention provides an endoscopic treatment system comprising a first insertion instrument, a second insertion instrument into which the first insertion instrument is inserted, and an observation device included in either the first insertion instrument or the second insertion instrument and used to observe a living-body tissue. The endoscopic treatment system further comprises: a clamping and lifting member that is included in the first insertion instrument and that has a claming member that clamps a living-body tissue that is an object of treatment and a lifting member that lifts the living-body tissue through bending; a tissue retaining member that is included in the second insertion instrument and that controls the position of the living-body tissue clamped and lifted by the clamping and lifting member included in the first insertion instrument or controls the lifting; a ligating member that ligates the living-body tissue whose position or lifting is controlled by the tissue retaining member; and a resecting member that resects the living-body tissue at a position between a region ligated by the ligating member and a region clamped by the clamping and lifting member.

Moreover, the second aspect of the present invention provides an endoscopic treatment method based on the endoscopic treatment system in accordance with the first invention. The endoscopic treatment method comprises the steps of: inserting a guide endoscope into an intended region in a living body's duct; inserting the second insertion instrument while mounting it on the outer surface of the endoscope; exchanging the endoscope for the first insertion instrument; clamping a living-body tissue through a lateral hole bored in the second insertion instrument; lifting the clamped living-body tissue using the first insertion instrument; ligating the lifted living-body tissue using the ligating member; resecting the ligated living-body tissue at a position between a ligated position and a clamper; and removing and collecting the resected living-body tissue together with the first insertion instrument.

The third aspect of the present invention provides an endoscopic treatment system comprising a first insertion instrument, a second insertion instrument into which the first insertion instrument is inserted, and an observing means included in either the first insertion instrument or the second insertion instrument and used to observe a living-body tissue. The endoscopic treatment system further comprises:

clamping and lifting means that is included in the first insertion instrument and that has clamping means which clamps a living-body tissue that is an object of treatment and lifting means which lifts the living-body tissue through bending; tissue retaining means that is included in the second insertion instrument and that controls the position of the living-body tissue clamped and lifted by the clamping and lifting means included in the first insertion instrument or controls the lifting; ligating means that ligates the living-body tissue whose position or lifting is controlled by the tissue retaining means; and resecting means that resects the living-body tissue at a position between a region ligated by the ligating means and a region clamped by the clamping and lifting means.

Namely, the endoscopic treatment system in accordance with the present invention comprises a first insertion instrument used to observe or lift an intended region, and a second insertion instrument used mainly-to ligate or resect the intended region. Furthermore, since a tissue is lifted by bending the first insertion instrument, a lesion is treated under endoscopic observation. The size of the tissue to be resected is adjusted by changing a height by which the tissue is lifted. Moreover, when the endoscopic treatment system comprising the first insertion instrument and second insertion instrument further comprises a third insertion instrument that is used to introduce endoscopic treatment means to a lesion, the maneuverability in insertion to a deep region in the large intestine is ensured.

The foregoing objects and other objects of the present invention and the advantages thereof will be clarified from the detailed description below.

According to the present invention, there is provided an endoscopic treatment system that ensures reliable insertion to any region over the whole length of the large intestine and that can ligate or resect all layers of an intended region under endoscopic observation.

BRIEF DESCRIPTION OF THE DRAWINGS

FIG. 4 is a sectional view along a 4-4 cutting-plane line shown in FIG. 3;

FIG. 5 is a sectional view along a 5-5 cutting-plane line shown in FIG. 3;

FIG. 6 is a sectional view along a 6-6 cutting-plane line shown in FIG. 3;

FIG. 7 is a perspective view showing a cutter and ligatures included in the distal part of the therapeutic instruments insertion aid included in the endoscopic treatment system shown in FIG. 1;

DETAILED DESCRIPTION OF THE PREFERRED EMBODIMENTS

To begin with, referring to FIG. 1 to FIG. 10, a first embodiment of an endoscopic treatment system in accordance with the present invention will be described below.

Figure 1:
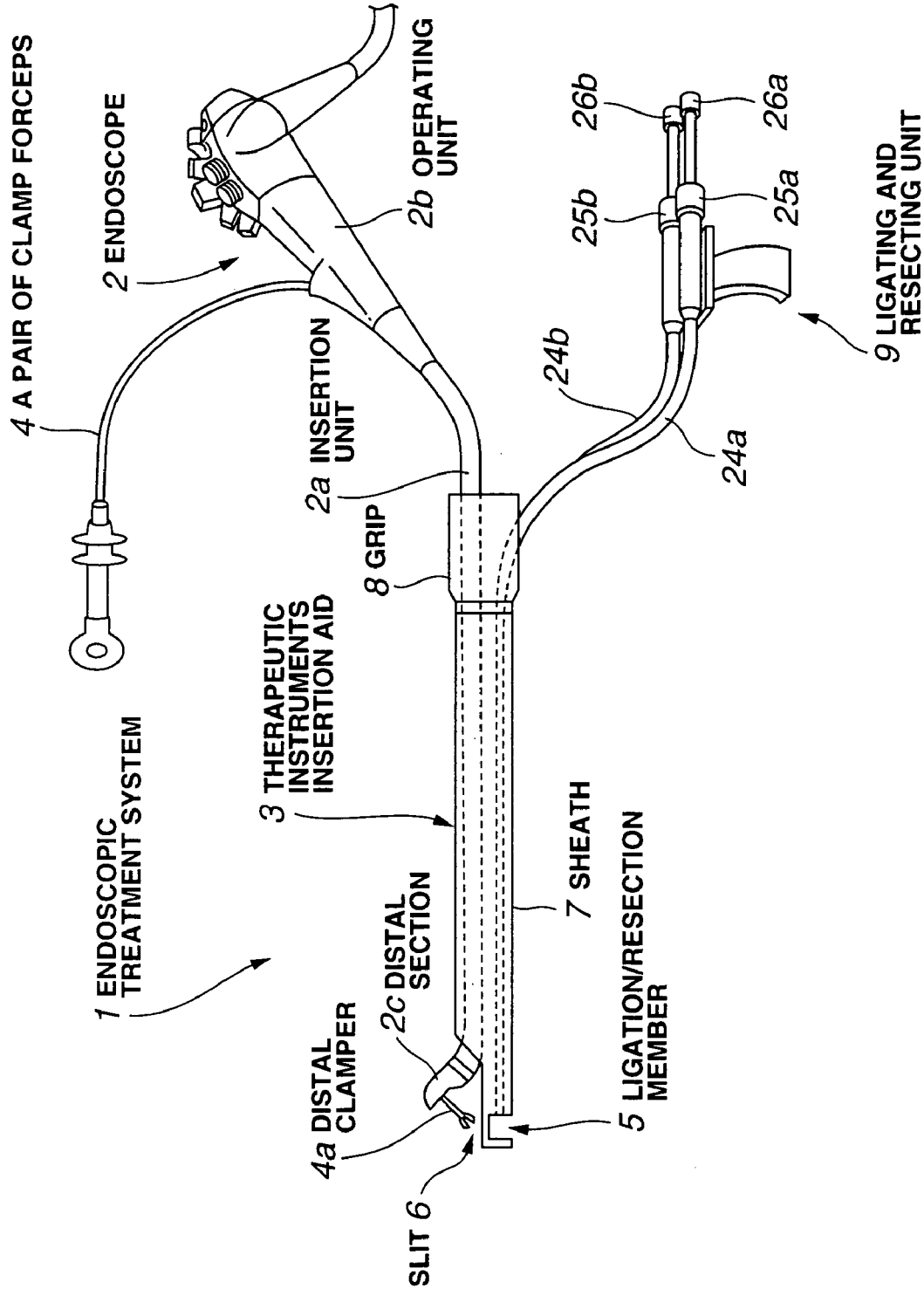
FIG. 1 shows the overall configuration of an endoscopic treatment system in accordance with a first embodiment of the present invention.

An endoscopic treatment system 1 in accordance with the first embodiment of the present invention comprises, as shown in FIG. 1, an endoscope 2 that is a first insertion instrument, and a therapeutic instruments insertion aid 3 that is a second insertion instrument. The endoscope 2 comprises an insertion unit 2a, an operating unit 2b formed at the proximal end of the insertion unit 2a, and a distal section 2c formed as the distal part of the insertion unit 2a. The insertion unit 2a is bendable and flexible. A plurality of operation wires, a control signal cable, a light guide cable, a water supply/suction or air supply/intake tube, and various kinds of probe channels lie through the insertion unit 2a. The operating unit 2b has: an operation knob that is handled in order to move the operation wires lying through the insertion unit 2a; functions used to couple the control signal cable, light guide cable, and water supply/suction or air supply/intake tube to a control signal source, an illumination light source, and a pump respectively; and a forceps channel insertion port. The distal section 2c includes: a bending portion that is bent vertically or laterally by handling the operation wires; an electronic image pickup device that irradiates illumination light from the distal end thereof and picks up the image of a subject illuminated with the illumination light; and an opening of the water supply/suction or air supply/intake tube and an opening for forceps.

A pair of clamp forceps 4 that is a claming member or claming means is inserted through the forceps channel insertion port formed in the operating unit 2b of the endoscope 2. A distal damper 4a formed as the distal parts of the pair of clamp forceps 4 is projected from the distal section 2c of the insertion unit 2a into a body cavity.

Incidentally, a forceps raiser that is not shown and used to deflect the projecting direction of the distal clamper 4a passed through the forceps channel is included in the distal section 2c of the endoscope 2. The forceps raiser is moved by handling a forceps raiser knob that is not shown and that is formed on the operating unit 2b. Moreover, the direction of a field of view offered by the endoscope 2 is a direction perpendicular to the longitudinal-axis direction of the endoscope 2 or a substantially backward direction.

The therapeutic instruments insertion aid 3 comprises a sheath 7, a grip 8, and a ligating and resecting unit 9. A passage channel through which the insertion unit 2a of the endoscope 2 is passed is formed throughout the grip 8 and sheath 7 alike.

The distal part of the sheath 7 of the therapeutic instruments insertion aid 3 has a slit 6 through which the distal section 2c of the insertion unit 2a of the endoscope 2 is projected, and a ligation/resection member 5. Moreover, the grip 8 of the therapeutic instruments insertion aid 3 has the ligating and resecting unit 9. The ligating and resecting unit 9 comprises linkage tubes 24a and 24b through which a cutter thrust wire 20 and a ligature thrust wire 21 (see FIG. 5) used to drive a cutter 17 and ligatures 18 (see FIG. 3) that will be described later and that are included in the ligation/resection member 5 are passed, and cylinders 25a and 25b and pistons 26a and 26b that are provided to the operator-side ends of the cutter thrust wire 20 and ligature thrust wire 21 respectively. Incidentally, the cylinders 25a and 25b and the pistons 26a and 26b are kept watertight and airtight.

Moreover, the sheath 7 of the therapeutic instruments insertion aid 3 has the flexibility permitting the sheath 7 to freely follow the bending of the insertion unit 2a of the endoscope 2. The sheath 7 is made of a relatively soft resin material, for example, polyurethane, vinyl chloride, polyurethane elastomer, polystyrene elastomer, polyolefin elastomer, polyester elastomer, polyamide elastomer, (porous) fluorocarbon resin, or any other thermoplastic elastomer. The sheath 7 has substantially the same length as the large intestine, or preferably, a length ranging from about 600 mm to about 1700 mm. Moreover, the therapeutic instruments insertion aid 3 has a valve, which is not shown and used to keep the therapeutic instruments insertion aid 3 airtight with the endoscope 2 passed through the therapeutic instruments insertion aid 3, included in the grip 8.

The structures of the ligation/resection member 5 and slit 6 in the distal part of the sheath 7 included in the therapeutic instruments insertion aid 3 will be described in conjunction with FIG. 2 to FIG. 6.

The slit 6 is formed in the substantially upper half of the distal part of the sheath 7 in the axial direction thereof. The slit 6 is formed such that the distal section 2c of the insertion unit 2a of the endoscope 2 inserted into the therapeutic instruments insertion aid 3 through the grip 8 will be projected from the slit 6.

The distal part 6f the sheath 7 has a lateral hole 10 that is formed in a side of the sheath opposite to the slit 6, that is, in the substantially lower part of the sheath in the axial direction thereof. Moreover, the distal part of the sheath 7 has a needle receiver 11 formed on the distal side of the lateral hole 10, and a ligature/cutter storage 12 formed on the operator side of the lateral hole 10.

The ligature/cutter storage 12 comprises a plurality of ligature storage holes 13 having a plurality of openings, and a cutter storage hole 14 having an opening whose width is substantially equal to or larger than the width of the plurality of openings (see FIG. 4). The cutter storage hole 14 is located more near to the slit 6 than the ligature storage hole 13 is. The cutter storage hole 14 and ligature storage hole 13 are preferably separated from each other by a dimension ranging from about 1 mm to about 5 mm.

Figure 3:
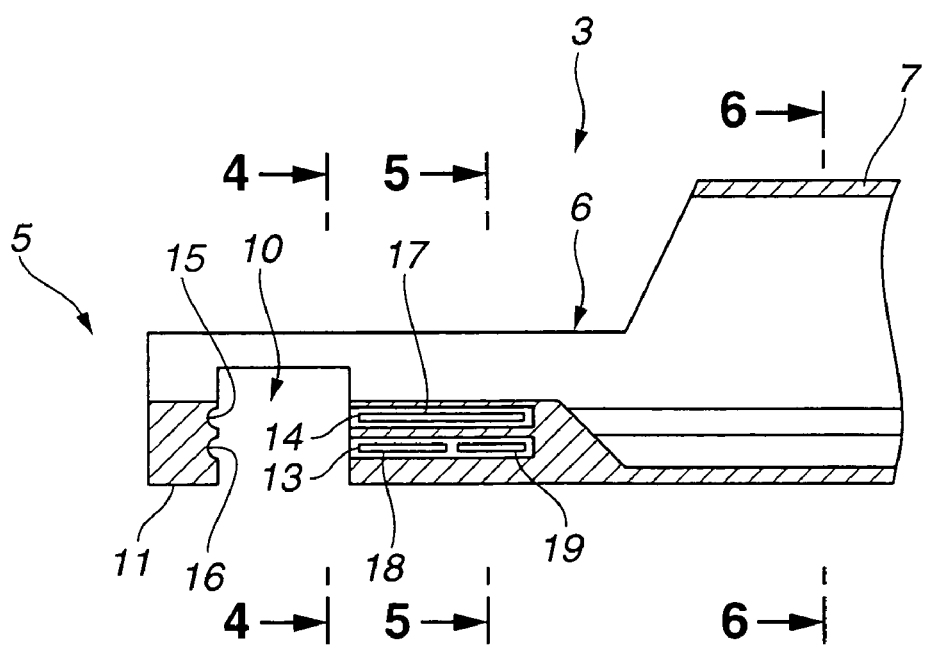
FIG. 3 is a sectional view along an axial cutting-plane line showing the distal part of the therapeutic instruments insertion aid included in the endoscopic treatment system shown in FIG. 1.

A cutter 17 that is a cutting means or a cutting member is, as shown in FIG. 3, accommodated in the cutter storage hole 14 such that the cutter 17 can freely slide. The distal end of the cutter thrust wire 20 is, as shown in FIG. 5, coupled to the cutter 17.

The ligatures 18 that are ligating means or a ligating member are accommodated in each of the openings of the ligature storage holes 13. Also, the distal part of the substantially plate-like ligature thrust member 19 of which distal end is divided into a plurality of portions such that it can thrust the respective ligatures 18 accommodated in the plurality of openings is accommodated in the ligature storage holes 13. The distal end of the ligature thrust wire 21 is coupled to the operator-side end of the ligature thrust member 19 (see FIG. 5 and FIG. 7).

The cutter thrust wire 20 and ligature thrust wire 21 are passed through and disposed in a cutter thrust wire lumen 22 and a ligature thrust wire lumen 23 which are formed in the internal wall of the sheath 7 in the axial direction thereof (see FIG. 6). The cutter thrust wire 20 and ligature thrust wire 21 are respectively connected by way of the linkage tubes 24a and 24b respectively extending from the grip 8 to the pistons 26a and 26b inside the cylinders 25a and 25b which are included in the ligating and resecting unit 9. Incidentally, the cylinders 25a and 25b and the pistons 26a and 26b are kept watertight and airtight.

A cutter receiving groove 15 and a needle receiving groove 16 are formed in a surface of the needle receiver 11 facing the lateral hole 10 such that they will be opposed to the cutter storage hole 14 and ligature storage holes 13 respectively.

Moreover, the ligatures 18 are, as shown in FIG. 7, staples shaped substantially like letter U. When the piston 26b is pushed into the cylinder 25b, the ligature thrust member 19 is thrust by way of the ligature thrust wire 21 connected to the piston 26b. The ligature thrust member 19 thrusts the ligatures 18 out of the ligature storage holes 13. Consequently, the ligatures 18 pierce an intended region caught in the lateral hole 10, and have the tips thereof bent by the needle receiver 11.

Furthermore, the cutter 17 has a resection blade edge, with which an intended region is resected, formed as a distal edge thereof. When the piston 26a is pushed into the cylinder. 25a, the cutter 17 is thrust out of the cutter storage hole 14 by way of the cutter thrust wire 20 connected to the piston 26a. Consequently, the intended region caught in the lateral hole 10 is resected.

Specifically, when the pistons 26a and 26b are pulled out to the greatest extent, the cutter 17, ligature thrust member 19, and ligatures 18 are accommodated in the cutter storage hole 14 and ligature storage holes 13 respectively. When the piston 26a is pushed into the cylinder 25a, the cutter 17 whose distal edge resects an intended region caught in the lateral hole 10 is abutted on the cutter receiving groove 15. When the piston 26b is pushed into the cylinder 25b, the tips of the ligatures 18 pierce a living-body tissue that is an intended region caught in the lateral hole 5, and abutted on the needle receiving groove 16 by means of the ligature thrust member 19. Incidentally, the spacing between the needle receiving groove 16 and the projected ligature thrust member 19 is set to a dimension permitting a gap, which is slightly narrower than the thickness of a living-body tissue to be ligated, to remain with the living-body tissue caught in the lateral hole. Namely, the gap between the tip of the ligature thrust member 19 and the needle receiving groove 16 is substantially double the thickness of the large intestine, or preferably, ranges from about 1 mm to about 5 mm.

Figure 2:
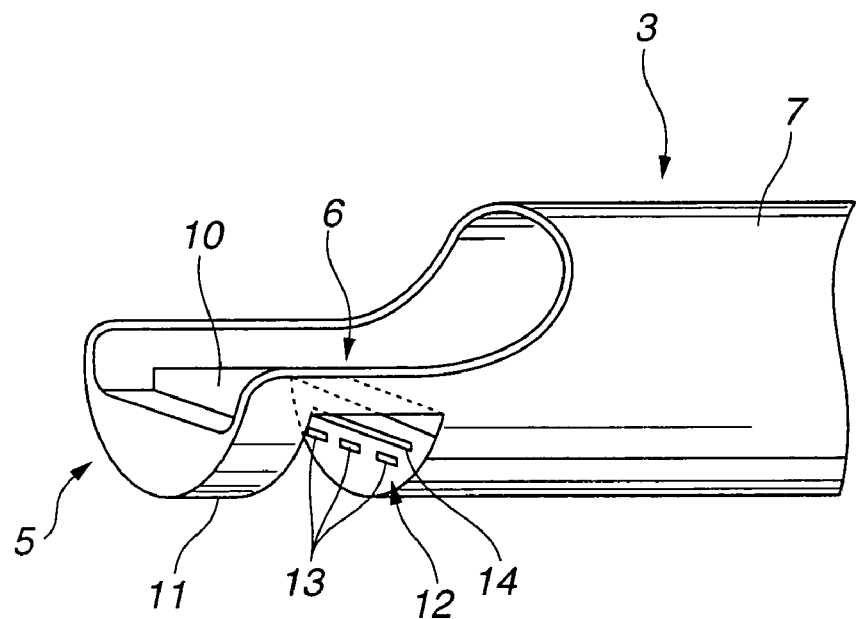
FIG. 2 is a perspective view showing the distal part of a therapeutic instruments insertion aid included in the endoscopic treatment system shown in FIG. 1.

Moreover, the slit 6 opposed to the lateral hole 10 has a width permitting the distal section 2c of the insertion unit 2a of the endoscope 2 to freely slide. The proximal end of the slit 6 is located more near to the operator side of the therapeutic instruments insertion aid than the lateral hole 10 is. The slit 6 extends by a length substantially identical to the length of the bending portion of the endoscope 2 from the center of the lateral hole 10. Preferably, the proximal end of the slit 6 is located at the operator-side end of the bending portion of the endoscope 2 when the endoscope 2 is positioned such that the distal end of the projected distal damper 4a is located substantially in the center of the lateral hole 10. At this time, the distal damper 4a is jutted out of the forceps passage channel running through the endoscope 2, the projecting direction of the distal damper 4a is deflected to the greatest extent using the forceps raiser, and the bending portion of the endoscope 2 is straightened substantially linearly. Moreover, the width of the slit is substantially identical to the outer diameter of the insertion unit 2a of the endoscope 2 or the inner diameter of the therapeutic instruments insertion aid 3. In the present embodiment, the width of the slit is substantially the same as the inner diameter of the therapeutic instruments insertion aid 3. Referring to FIG. 2 to FIG. 4, the slit occupies approximately a half of a section of the therapeutic instruments insertion aid vertical to the sheet of paper showing the drawings.

The ligatures 18 are shaped substantially like letter U using a thin wire-like metallic member. When the ligature thrust member 19 is thrust, the feet of the ligatures 18 are abutted on the needle receiving groove 16 and bent inward to have a substantially square shape.

Figure 8:
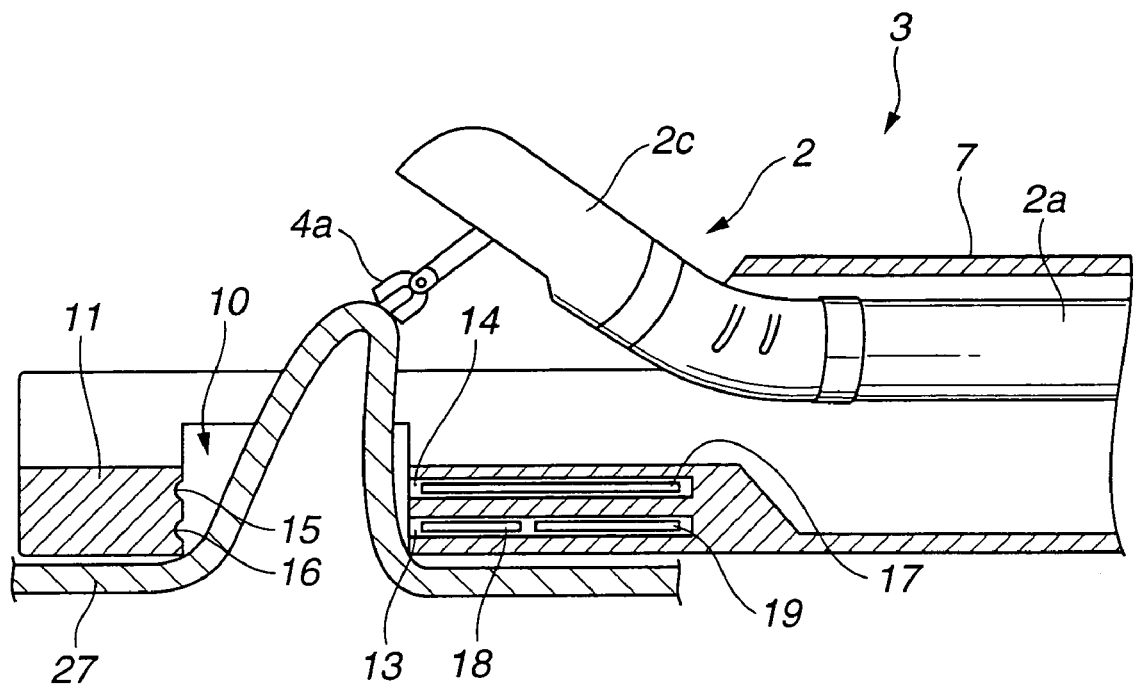
FIG. 8 is an explanatory diagram showing lifting of an intended region using the endoscopic treatment system shown in FIG. 1.
Figure 9:
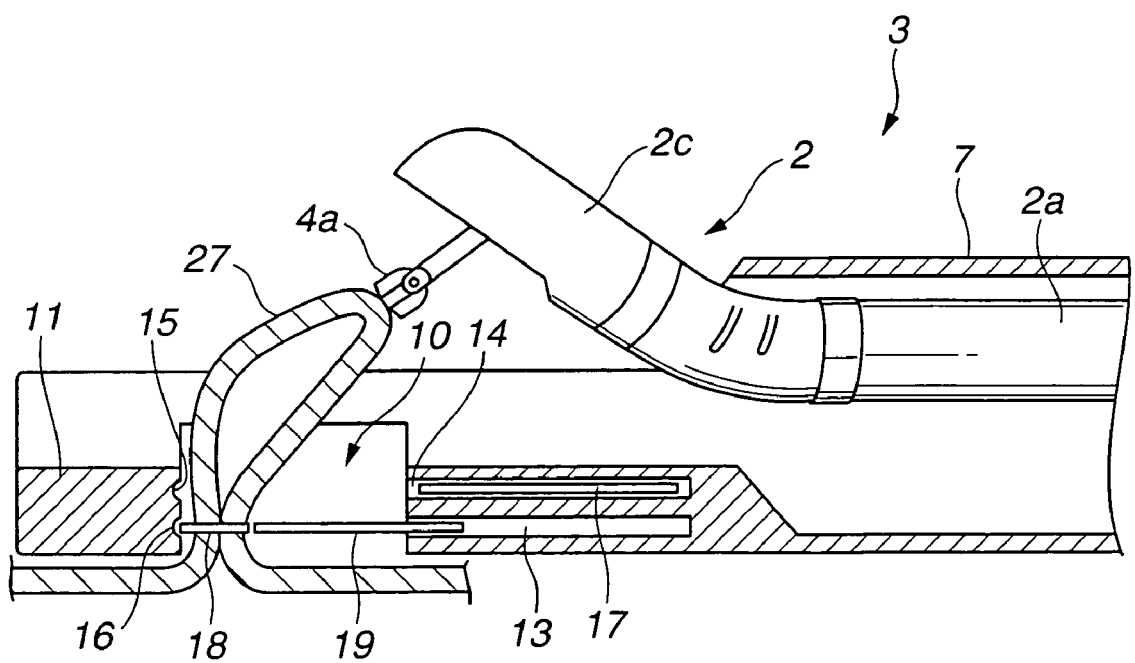
FIG. 9 is an explanatory diagram showing ligation of an intended region using the endoscopic treatment system shown in FIG. 1.
Figure 10:
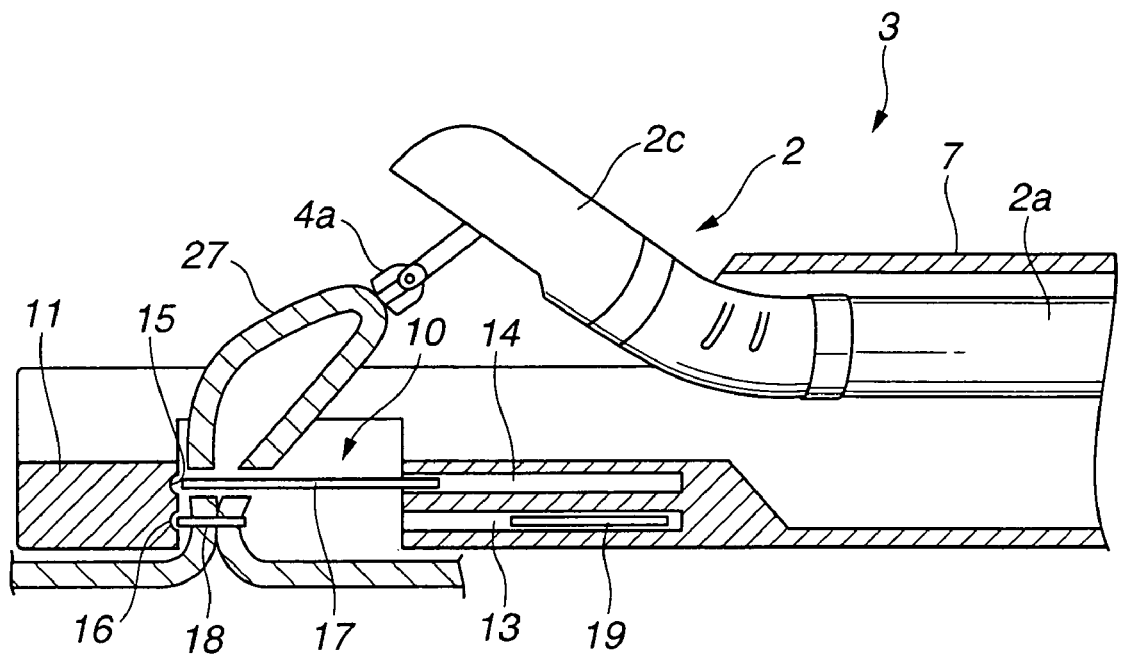
FIG. 10 is an explanatory diagram showing resection of an intended region using the endoscopic treatment system shown in FIG. 1.

Treating an intended region in the large intestine or the like using the endoscopic treatment system will be described in conjunction with FIG. 8, FIG. 9, and FIG. 10.

To begin with, the therapeutic instruments insertion aid 3 is mounted on the outer surface of a large intestinal endoscope that is not shown. Thereafter, the large intestinal endoscope is inserted into an intended region in the large intestine. Thereafter, the therapeutic instruments insertion aid 3 is moved along the outer surface of the insertion unit of the large intestinal endoscope and thus inserted into the intended region. Upon the therapeutic instruments insertion aid 3 being inserted to the intended region while being moved along the outer surface of the large intestinal endoscope, the large intestinal endoscope is removed from the therapeutic instruments insertion aid 3. The endoscope 2 is then inserted into the therapeutic instruments insertion aid 3 from which the large intestinal endoscope has been removed. With the endoscope 2 inserted into the therapeutic instruments insertion aid 3 that is inserted into the intended lesion in the large intestine, the lateral hole 10 of the therapeutic instruments insertion aid 3 is aligned with the intended region within the field of view offered by the endoscope 2. Upon the intended region being aligned with the lateral hole 10 of the therapeutic instruments insertion aid 3, the distal damper 4a is handled in order to clamp and lift the large intestine 27 through the lateral hole 10. The lifting is achieved by bending the bending portion of the endoscope 2. Namely, the bending portion of the endoscope 2 fills the role of lifting means for lifting the large intestine 27 that is a living-body tissue clamped with the distal damper 4a (see FIG. 8).

The piston 26a is pushed into the cylinder 25a while the intended region in the large intestine caught in the lateral hole 10 is being clamped and lifted with the distal damper 4a. The ligature thrust member 19 connected to the distal end of the ligature thrust wire 21 is thrust forward according to the degree of the pressing of the piston 26a. Moreover, the ligatures 18 are thrust into a position near the intended region in the large intestine 27 by means of the ligature thrust member 19. Consequently, the feet of the U-shaped ligatures 18 pierce all the layers of the large intestine 27. Moreover, the feet of the ligatures 18 are abutted on the needle receiving groove 16 and bent inward. Consequently, the ligatures 18 are shaped like a square to ligate all the layers of the large intestine 27 (see FIG. 9). The ligature thrust member 19 fills the role of tissue retaining means or a tissue retaining member for controlling the position of a living-body tissue clamped by the distal clamper 4a or the lifting of the living-body tissue.

After the large intestine 27 clamped and lifted with the endoscope 2 is ligated through the lateral hole 10 using the ligatures 18, the piston 26b is pushed into the cylinder 25b. The cutter 17 connected to the distal end of the cutter thrust wire 20 is thrust forward according to the degree of the pressing of the piston 26b. With the cutter 17 thrust forward, all the layers of the large intestine 27 are resected at a position near a portion of the large intestine ligated with the ligatures 18 (see FIG. 10).

Specifically, within the field of view offered by the endoscope 2, the center of the intended region in the large intestine 27 is clamped and lifted through the distal lateral hole 10 of the therapeutic instruments insertion aid 3 using the distal damper 4a. All the layers of the clamped and lifted large intestine are ligated using the ligatures 18. The ligated large intestine 27 is resected using the cutter 17.

As mentioned above, an intended lesion is clamped and lifted while being identified under observation through the endoscope. All the layers of the intended region clamped and lifted are circumferentially ligated using the ligatures 18. Thereafter, the intended region is resected at a position near the ligated portion using the cutter 17. A puncture or the like will not take place. The intended region can be reliably resected with a circumferential margin left. Furthermore, the slit 6 is formed in the distal part of the therapeutic instruments insertion aid 3. Consequently, the range within which the distal section 2c of the endoscope 2 can be raised is expanded, and ligation or resection can be performed within a wide field of view without the necessity of increasing the outer diameter of the therapeutic instruments insertion aid 3. Moreover, the resected range of a living-body tissue can be arbitrarily adjusted by changing the degree of clamping or lifting to be performed by a pair of clamp forceps.

Incidentally, the endoscope 2 included in the first embodiment is a side-vision endoscope. Alternatively, an oblique-vision endoscope may be substituted for the side-vision endoscope. When the upper side of an image displayed on a monitor used in combination with the side-vision or oblique-vision endoscope is associated with the distal end of an endoscope, an endoscopic treatment system allows an operator to treat a lesion while looking down at the lesion.

Figure 11:
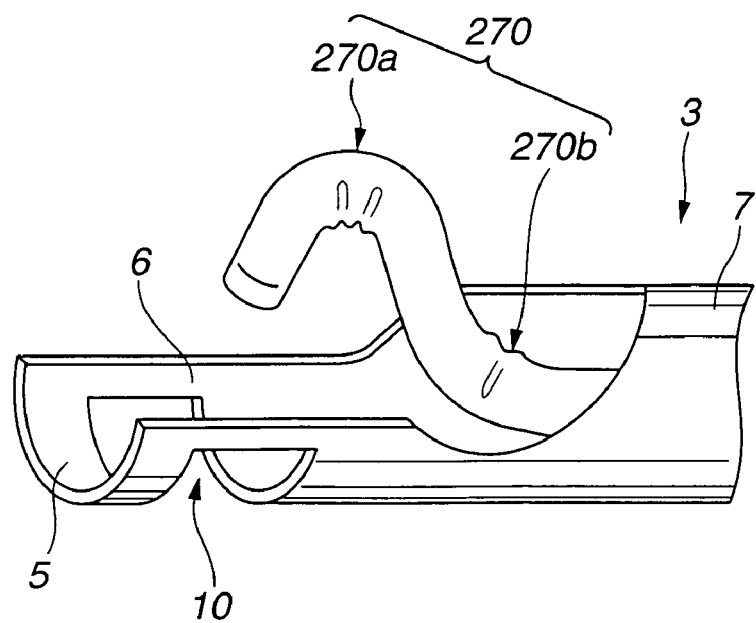
FIG. 11 is a perspective view showing another form of the therapeutic instruments insertion aid included in the endoscopic treatment system shown in FIG. 1.

The distal section 2c of the endoscope 2 may use the distal section of an endoscope 270 in which two or more bending portions 270a and 270b can be mutually independently bent as another embodiment shown in FIG. 11. In this case, the range within which a tissue of the large intestine can be lifted is expanded.

Next, an endoscopic treatment system 31 in accordance with a second embodiment of the present invention will be described in conjunction with FIG. 12 to FIG. 24.

Figure 12:
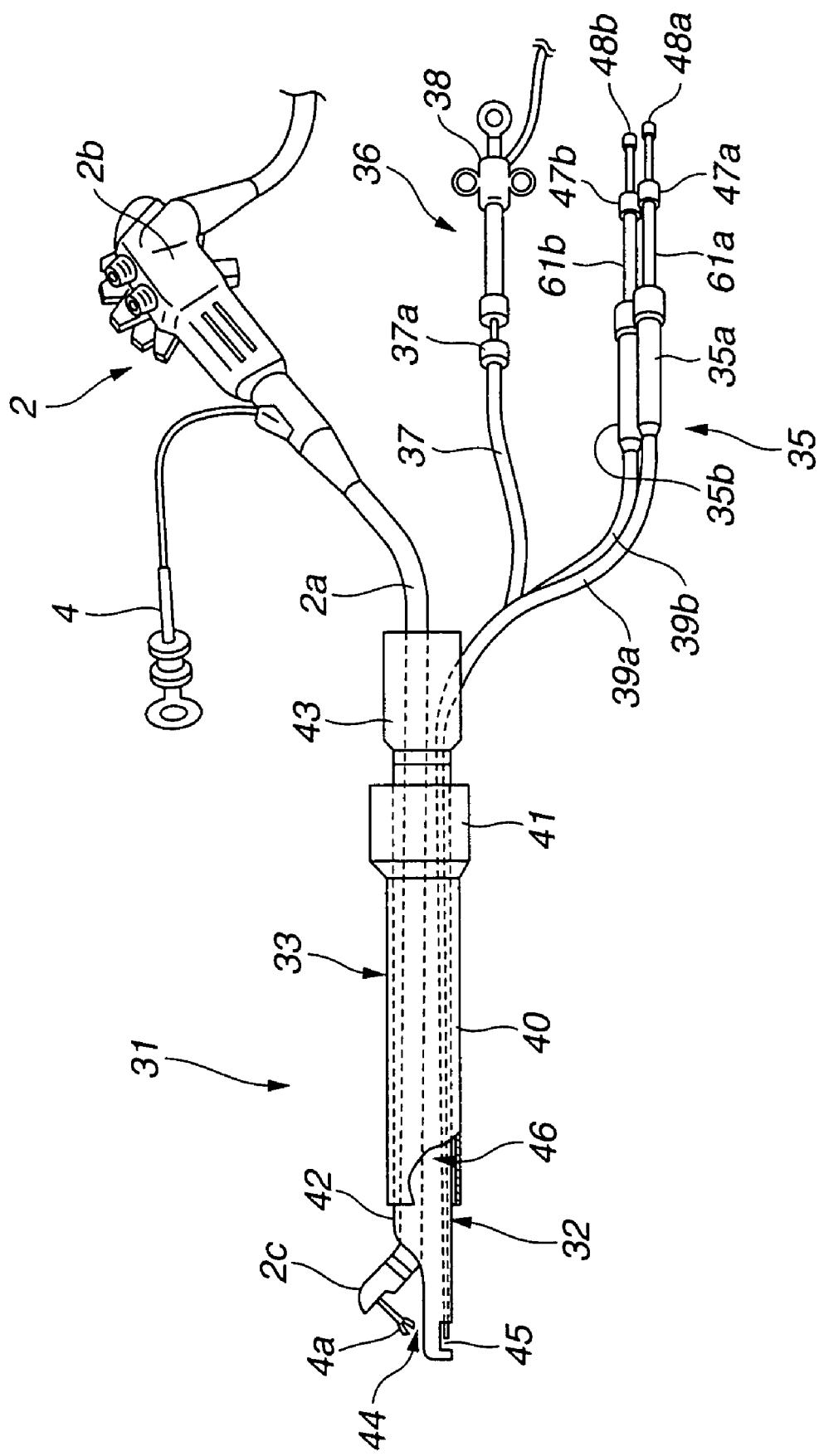
FIG. 12 shows the overall configuration of an endoscopic treatment system in accordance with a second embodiment of the present invention.

The endoscopic treatment system 31 of the second embodiment comprises: as shown in FIG. 12, an endoscope 2 that is a first insertion instrument; a therapeutic instruments insertion aid 32 that is a second insertion instrument through which the endoscope 2 is passed; and a system insertion aid 33 that is a third insertion instrument that helps the endoscope 2 and therapeutic instruments insertion aid 32 reach an intended region in a living body's duct.

The endoscope 2 comprises an insertion unit 2a, an operating unit 2b formed at the proximal end of the insertion unit 2a, and a distal section 2c that is the distal part of the insertion unit 2a. The insertion unit 2a is bendable and flexible. A plurality of operation wires, a control signal cable, a light guide cable, a water supply/suction or air supply/intake tube, and various kinds of probe channels are run through the insertion unit 2a. The operating unit 2b has: an operation knob that is handled in order to move the operation wires lying through the insertion unit 2a; functions used to couple the control signal cable, light guide cable, and water supply/suction or air supply/intake tube to a control signal source, an illumination light source, and a pump respectively; and a forceps channel insertion port. The distal section 2c has: a bending portion that is bent vertically or laterally by handling the operation wires; an electronic image pickup device that irradiates illumination light from the distal end thereof and picks up the image of subject illuminated with the illumination light; and an opening of the water supply/suction or air supply/intake tube and an opening for forceps.

A pair of clamp forceps 4 is inserted through the forceps channel insertion port formed in the operating unit 2b of the endoscope 2. A distal damper 4a formed as the distal part of the pair of clamp forceps 4 is projected into a body cavity through the distal section 2c of the insertion unit 2a.

A forceps raiser that is not shown and intended to deflect the projecting direction of the distal clamper 4a passed through a forceps channel is included in the distal section 2c of the endoscope 2. The forceps raiser is moved by handling a forceps raising knob that is not shown and formed on the operating unit 2b. The direction of the field of view offered by the endoscope 2 is a direction perpendicular to the longitudinal-axis direction of the endoscope 2 or a substantially backward direction. Namely, the endoscope 2 is a side-vision endoscope.

The therapeutic instruments insertion aid 32 comprises: a sheath 42; a grip 43; a slit 44 which is formed in the distal part of the sheath 42 and in which the distal section 2c of the endoscope 2 and the distal damper 4a projecting from the distal section 2c are located; and a lateral hole 45 provided on the reverse side of the slit 44. Furthermore, the therapeutic instruments insertion aid 32 has: a passage channel, not shown, through which the endoscope 2 inserted from the grip 43 is passed to the sheath 42; and passage channels through which puncturing needles 49a and 49b and a cutter metallic loop wire 55 which are moved by handling a needle slider unit 35 and a cutter unit 36 that will be described later are passed (see FIG. 13).

The system insertion aid 33 comprises a sheath 40 and a grip 41. A system passage channel 46 through which the therapeutic instruments insertion aid 32 is passed is extended from the grip 41 over through the sheath 40.

The sheath 42 of the therapeutic instruments insertion aid 32 and the sheath 40 of the system insertion aid 33 have the flexibility permitting the sheathes to freely follow the bending of the insertion unit 2a of the endoscope 2. The sheath 42 and sheath 40 are made of a relatively soft resin material, for example, polyurethane, vinyl chloride, polyurethane elastomer, polystyrene elastomer, polyolefin elastomer, polyester elastomer, polyamide elastomer, (porous) fluorocarbon resin, or any other thermoplastic elastomer. The sheath 42 and sheath 40 have substantially the same length as the large intestine, or preferably, ranges from about 600 mm to about 1700 mm.

Moreover, the grip 41 of the system insertion aid 33 has a valve, which is not shown, for the purpose of keeping the system insertion aid 33 watertight when the therapeutic instruments insertion aid 32, through which the endoscope 2 is passed, run through the system insertion aid 33.

The needle slider unit 35 and the cutter unit 36 that are handled in order to move the puncturing needles 49a and 49b (see FIG. 13) to be described later are connected to the grip 43 of the therapeutic instruments insertion aid 32.

The needle slider unit 35 comprises: needle introduction tubes 39a and 39b through which the two puncturing needles 49a and 49b included in the therapeutic instruments insertion aid 32 are passed; needle sliders 35a and 35b to which the proximal ends of the needle introduction tubes 39a and 39b are connected and fixed; needle sheathes 61a and 61b that are inserted into the needle sliders 35a and 35b and that sheath the puncturing needles 49a and 49b; puncturing needle thrust stoppers 47a and 47b formed at the proximal ends of the needle sheathes 61a and 61b; and pusher wire stoppers 48a and 48b (to be described later) used to thrust a ligation needle by way of the puncturing needle thrust stoppers 47a and 47b, needle sheathes 61a and 61b, needle slider 35a and 35b, needle introduction tubes 39a and 39b, and puncturing needles 49a and 49b.

Specifically, when the needle sheathes 61a and 61b are pushed into the needle sliders, the puncturing needles 49a and 49b are thrust forward. When the pusher wire stoppers 48a and 48b are pushed, ligation needles borne by the puncturing needles 49a and 49b is thrust forward.

The cutter unit 36 comprises: a cutter introduction tube 37 through which the resection metallic loop wire 55 (see FIG. 13) included in the distal part of the therapeutic instruments insertion aid 42 is passed; a stopper 37a to which the proximal end of the cutter introduction tube 37 is connected; and a handle 38 to which the proximal end of the resection metallic loop wire 55 is connected.

Specifically, when a handle 38 is pulled out, the resection metallic loop wire 55 is led inward in order to hold an intended region.

The slit 44 is formed as substantially the upper half of the distal part of the sheath 42 of the therapeutic instruments insertion aid 32 in the axial direction of the sheath 42. The slit 44 is formed such that the distal section 2c of the insertion unit 2a of the endoscope 2 inserted from the grip 43 of the therapeutic instruments insertion aid 32 will project through the slit. A forceps raiser that is not shown is located in the slit 44.

Moreover, the distal part of the sheath 42 has the lateral hole 45, which is an opening formed substantially in the lower half of the distal part in the axial direction of the sheath 44, opposed to the slit 44.

The structure of the distal part of the sheath 42 of the therapeutic instruments insertion aid 32 including the puncturing needles 49a and 49b and resection metallic loop wire 55 will be described in conjunction with FIG. 13 to FIG. 16 below.

Figure 16:
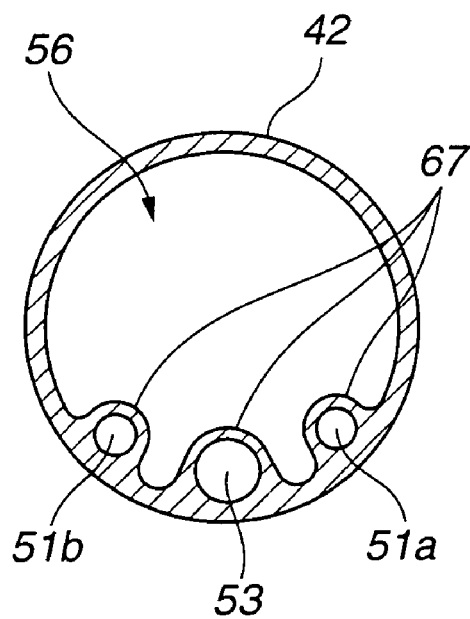
FIG. 16 is a sectional view of a cutting plane orthogonal to the axial direction of an endoscope passage channel included in the therapeutic instruments insertion aid shown in FIG. 13.

An endoscope passage channel 56, puncturing needle passage channels 51a and 51b, and a cutter passage channel 53 are formed as integral parts inside the sheath 42 of the therapeutic instruments insertion aid 32. The endoscope passage channel 56, puncturing needle passage channels 51a and 51b, and cutter passage channel 53 are, as shown in FIG. 16, separated from one another with partitions 67. Moreover, the puncturing needle passage channels 51a and 51b are substantially parallel to each other. The center axis of the cutter passage channel 53 is located substantially in the middle of the puncturing needle passage channels 51a and 51b.

The sheath 42 having the endoscope passage channel 56, puncturing needle passage channels 51a and 51b, and cutter passage channel 53 is formed as follows: an elongated sheath member having the endoscope passage-channel 56, puncturing needle passage channels 51a and 51b, and cutter passage channel 53 is formed; the elongated sheath member is cut to be the sheath 42 having a predetermined length; the endoscope passage channel 56 is cut by a predetermined length from the distal end of the sheath 42, which has the predetermined length, in the longitudinal-axis direction of the sheath 42 in order to form the slit 44; the partitions 67 of the puncturing needle passage channels 51a and 51b and cutter passage channel 53 are cut partially by the predetermined length from the distal end of the sheath 42 in the longitudinal-axis direction of the sheath 42; and the lateral hole 45 is cut through at a position opposite to the position of the slit 44 at which the partitions 67 are cut away.

At this time, the end of the cutter passage channel 53 is disposed at the distal end of the sheath 42. The ends of the puncturing needle passage channels 51a and 51b are aligned with each other and disposed behind the end of the cutter passage channel 53, on the operator side of the therapeutic instruments insertion aid.

The lateral hole 45 is located between the distal end of the cutter passage channel 53 and the distal end of the sheath 42. The center axis of the lateral hole 45 is located substantially in the middle of the two puncturing needle passage channels 51a and 51b. The width of the lateral hole 45 is larger at least than the spacing between the two puncturing needle passage channels 51a and 51b. The side edges of the lateral hole 45 are located outside the two puncturing needle passage channels 551a and 51b.

The puncturing needle passage channels 51a and 51b are substantially parallel to each other. The inner diameter of the puncturing needle passage channels 51a and 51b is determined such that the puncturing needles 49a and 49b can freely slide therein. Moreover, the spacing between the tips of the puncturing needles 49a and 49b lying through the puncturing needle passage channels 51a and 51b respectively is set to a constant value ranging from 2 mm to 20 mm.

Slits 50a and 50b are formed in the puncturing needles 49a and 49b respectively in the longitudinal-axis directions thereof. Slits 52a and 52b whose proximal ends are located at positions substantially corresponding to the proximal ends of the slits 50a and 50b of the puncturing needles 49a and 49b respectively are formed in the puncturing needle passage channels 51a and 51b respectively.

Figure 14:
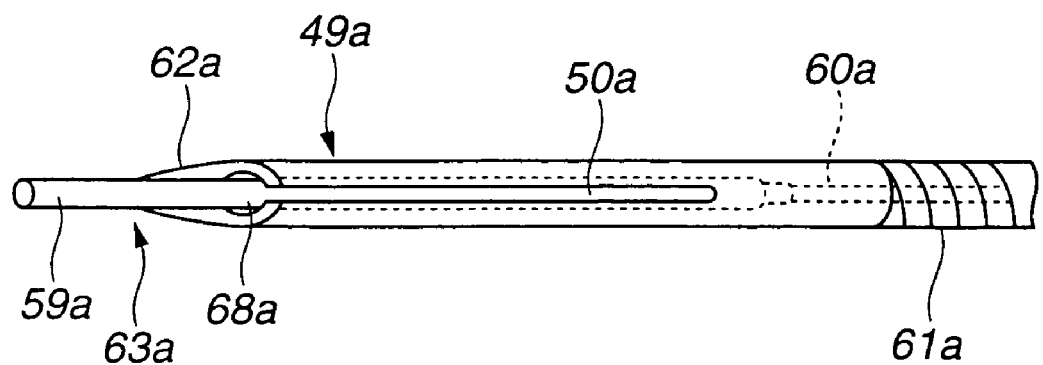
FIG. 14 shows the structure of a puncturing needle disposed in the distal part of the therapeutic instruments insertion aid shown in FIG. 13.

The structure of the puncturing needles 49a and 49b will be detailed in conjunction with FIG. 14. Since the puncturing needles 49a and 49b have the same structure, the puncturing needle 49a will be described for instance. The puncturing needle 49a has: a needle sheath 61a formed with a hollow cylindrical member; a needle portion 62a that is the sharpened distal part of the needle sheath 61a; and the slit 50a having been cut through by a predetermined length in the longitudinal-axis direction of the needle sheath 61a from the needle portion 62a.

A substantially bar-like projectile member 59a is put in the needle sheath 61a of the puncturing needle 49a such that it can slide freely. The pusher wire 60a formed with a metallic wire made of a stainless steel or the like is connected to the proximal end of the projectile member 59a. The projectile member 59a and pusher wire 60a constitute a ligation unit pusher 63a.

The proximal end of the pusher wire 60a is connected to the pusher wire stopper 48a or 48b included in the needle slider unit 35.

Figure 13:
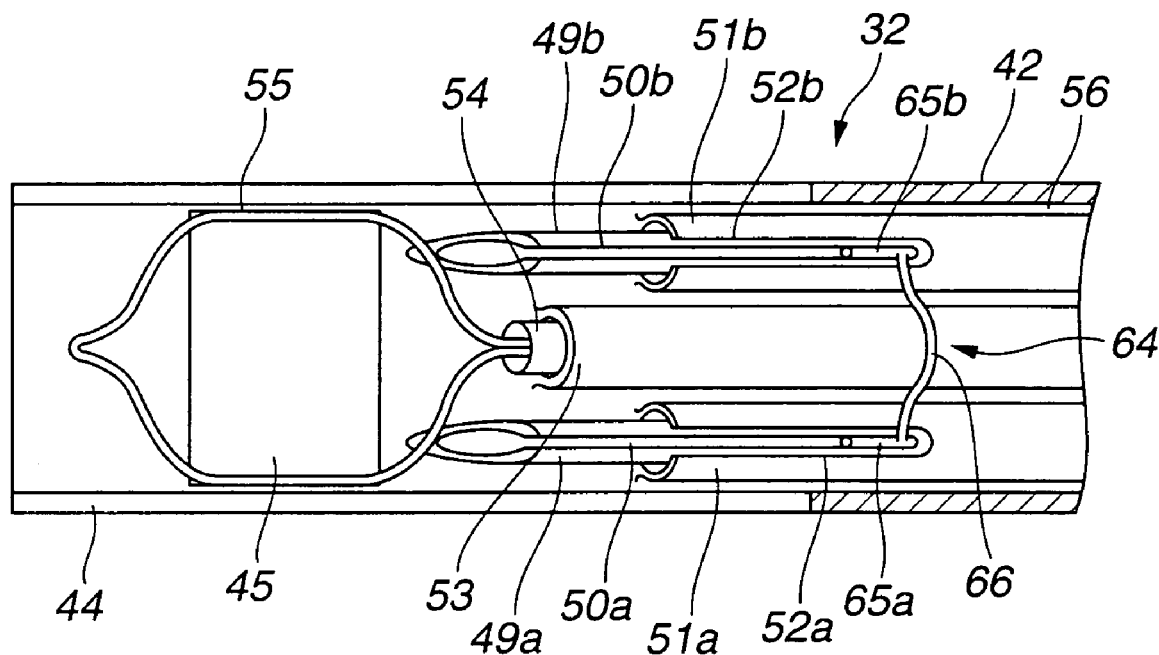
FIG. 13 shows the components incorporated in the distal part of a therapeutic instruments insertion aid included in the endoscopic treatment system shown in FIG. 12.

Moreover, the pusher wire stoppers 48a and 48b included in the needle slider unit 35 are pulled out in order to pull out the pusher wires 60a and 60b and the projectile members 59a and 59b into the operator sides of the puncturing needles 49a and 49b. At this time, a ligation unit 64 is, as shown in FIG. 13, put in the slits 50a and 50b of the puncturing needles 49a and 49b.

Figure 15:
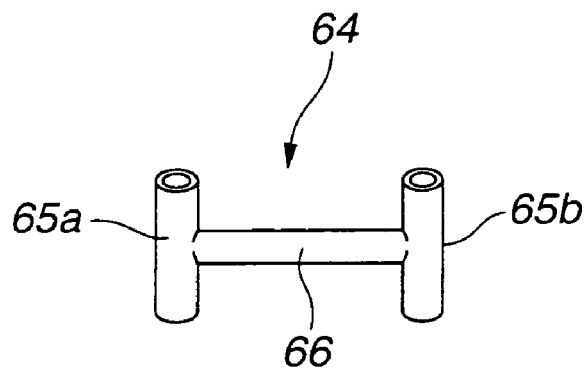
FIG. 15 is a perspective view showing a ligation unit employed in the therapeutic instruments insertion aid shown in FIG. 13.

The ligation unit 64 looks, as shown in FIG. 15, like letter H as a whole and comprises T bars 65a and 65b that are substantially cylindrical, and a T bar sheath 66 that links the T bars 65a and 65b substantially in the center of the ligation unit. The T bar sheath 66 is thinner than the T bars 5a and 65b, and has a length covering substantially the four layers of the large intestine to be ligated. The length of the T bars 65a and 65b permits covering of all the layers and ranges from about 5 mm to about 15 mm, or preferably about 10 mm.

The ligation unit 64 is formed with a relatively soft resin material, for example, polyurethane, vinyl chloride, polyurethane elastomer, polystyrene elastomer, polyolefin elastomer, polyester elastomer, polyamide elastomer, (porous) fluorocarbon resin, or any other thermoplastic elastomer.

Consequently, the puncturing needle 49a has the T bar 65a included in the ligation unit 64 (see FIG. 13) and the ligation unit pusher 63a (see FIG. 14) incorporated therein such that they can freely slide. Moreover, the puncturing needle 49a has a ligation unit passage channel 68a formed therein to extend from the needle member 62a of the puncturing needle 49a to the operator side thereof.

When the T bar 65a is put from the distal end of the needle member 62a, the T bar sheath 66 is arranged freely slidably in the direction of the slit 50a. Namely, the slit 50a has a width disabling the T bar 65a and projectile member 59a from passing through the slit 50a. The length of the slit 50a is set to a value disabling one end of the T bar 65a from being exposed from the distal end of the puncturing needle 49a when the joint of the T bar 65a and T bar sheath 66 is located at the proximal end of the slit 50a. When the puncturing needle 49a is fully projected, the tip of the puncturing needle 49a is located forward beyond the distal side of the lateral hole 45. However, the proximal end of the slit 50a is to be located at a position separated from the tip of the puncturing needle 49a by substantially the same length as the thickness of the tissues of the large intestine pierced by the puncturing needle.

The needle member of the puncturing needle 49a is formed with a metallic pipe whose material is a stainless steel or Nitinol, and has a needle tip shaped such that the needle tip can pierce intracavitary tissues. The inner diameter of the needle member ranges from about 0.5 mm to 1.5 mm and the outer diameter thereof ranges from about 0.7 mm to 2.0 mm.

The needle sheath 61a is formed with a resin tube made of, for example, a fluorocarbon resin, polyethylene, polyamide, polyimide, polyurethane, or any other thermoplastic elastomer, or a metallic coil. The metallic coil may be sheathed with a resin tube. Otherwise, a resin tube having a metallic mesh embedded therein for fear the metallic coil may be buckled easily will do.

FIG. 13 shows the puncturing needles 49a and 49b and the ligation unit 64 set in the therapeutic instruments insertion aid 32. The T bars 65a and 65b of the ligation unit 64 are put in the slits 50a and 50b of the puncturing needles 49a and 49b respectively. The puncturing needles 49a and 49b are put in the puncturing needle channels 51a and 51b respectively. At this time, the T bar sheath 66 is passed through the slits 50a and 50b and the slits 52a and 52b.

Referring to FIG. 13, the tips of the puncturing needles 49a and 49b are projected from the puncturing needle channels 51a and 51b respectively. In reality, preferably, the proximal ends of the slits 52a and 52b are located on the operator sides of the puncturing needle channels, and the tips of the puncturing needles 49a and 49b are enclosed in the puncturing needle channels 51a and 51b respectively.

The proximal ends of the needle sheaths 61a and 61b are passed through the needle introduction tubes 39a and 39b, which extend from the grip 43, and the needle sliders 35a and 35b, and then connected to the puncturing needle thrust stoppers 47a and 47b respectively. The needle sliders 35a and 35b each has a valve that is not shown and used to keep the inside of the needle slider airtight when the needle sheath 61a or 61b are inserted thereinto. Moreover, the pusher wires 60a and 60b are inserted through the needle sheaths 61a and 61b and the puncturing needle thrust stoppers 47a and 47b respectively. The needle sheaths 61a and 61b and the puncturing needle thrust stoppers 47a and 47b each have a valve that keeps the inside thereof airtight. The pusher wires 60a and 60b are connected to the pusher wire stoppers 48a and 48b respectively.

When the needle sheaths 61a and 61b are fully pulled out of the needle sliders 35a and 35b respectively, the tips of the puncturing needles 49a and 49b are located respectively in the proximal ends rather than distal ends of the puncturing needle channels 51a and 51b. When the needle sheaths 61a and 61b are fully pushed into the needle sliders 35a and 35b respectively, the tips of the puncturing needles 49a and 49b are located beyond the distal side of the lateral hole 45. At this time, if the length by which the puncturing needles 49a and 49b are projected from the distal side of the lateral hole 45 is 10 mm or more, the puncturing needles 49a and 49b easily pierce the large intestine led into the lateral hole 45. Preferably, the length is about 20 mm.

Referring to FIG. 13, a sheath 54 is substantially projected from the cutter passage channel 53. The metallic loop wire 55 is projected from the sheath 54 and disposed to encircle the lateral hole 45. The sheath 54 is connected to the stopper 37a by way of the cutter passage channel 53 and cutter introduction tube 37. The proximal end of the metallic loop wire 55 is connected to the handle 38 via the stopper 37a. The stopper 37a and loop wire 55 are kept airtight. Moreover, a high-frequency power supply unit that is not shown is connected to the handle 38.

Resecting all the layers of the large intestine to be performed using the endoscopic treatment system in accordance with the second embodiment having the foregoing components will be described in conjunction with FIG. 17 to FIG. 22.

Figure 17:
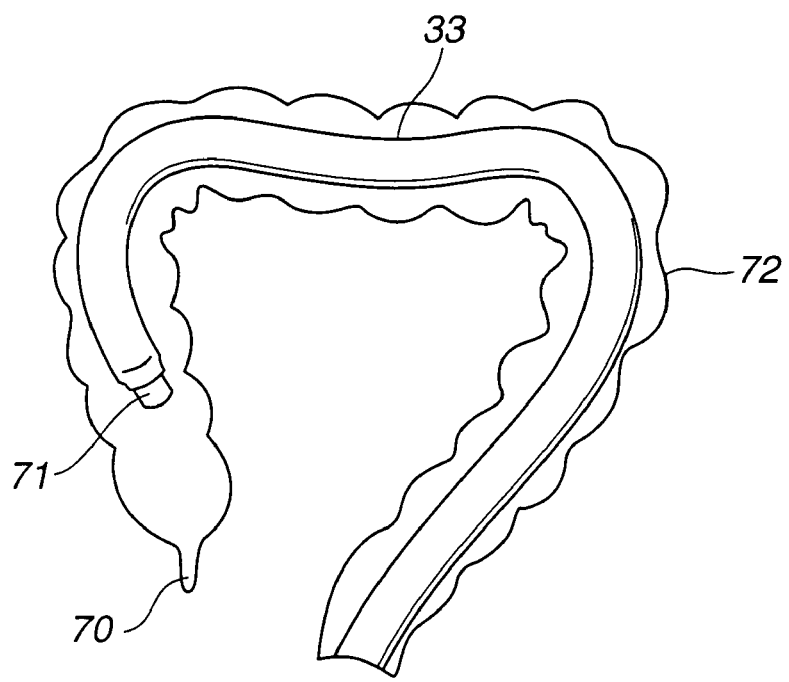
FIG. 17 is an explanatory diagram showing insertion of the therapeutic instruments insertion aid, which is included in the endoscopic treatment system shown in FIG. 12, into the large intestine.
Figure 18:
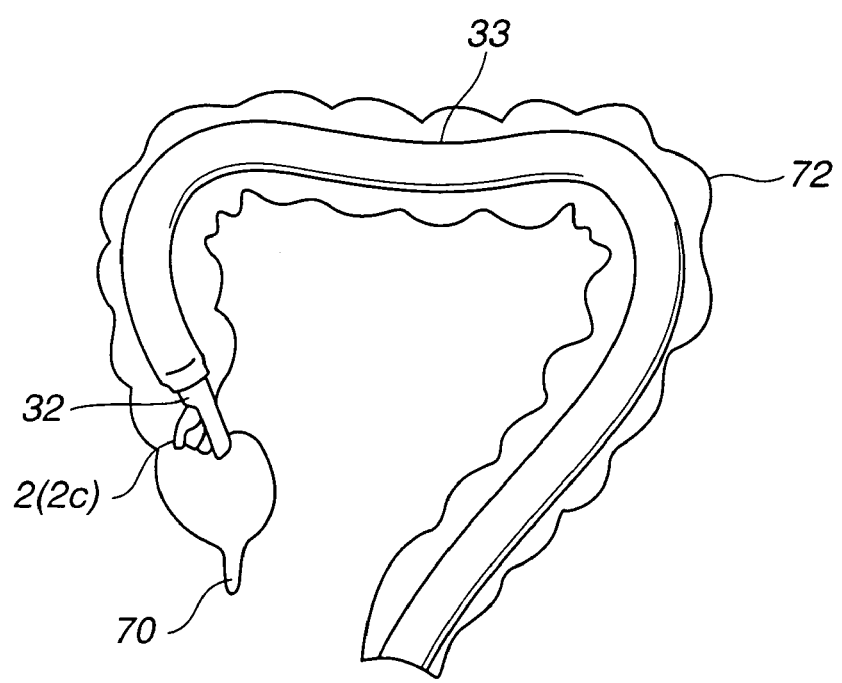
FIG. 18 is an explanatory diagram showing insertion of the therapeutic instruments insertion aid, which is included in the endoscopic treatment system shown in FIG. 12, into the large intestine.
Figure 19:
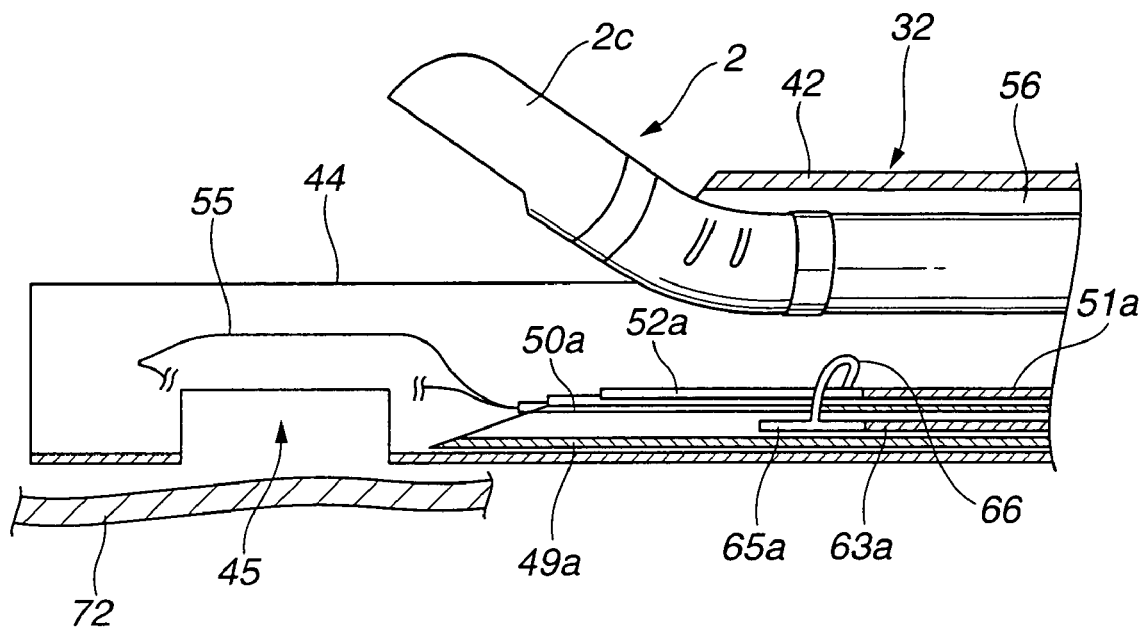
FIG. 19 is an explanatory diagram showing insertion into an intended region performed using the endoscopic treatment system shown in FIG. 12.
Figure 20:
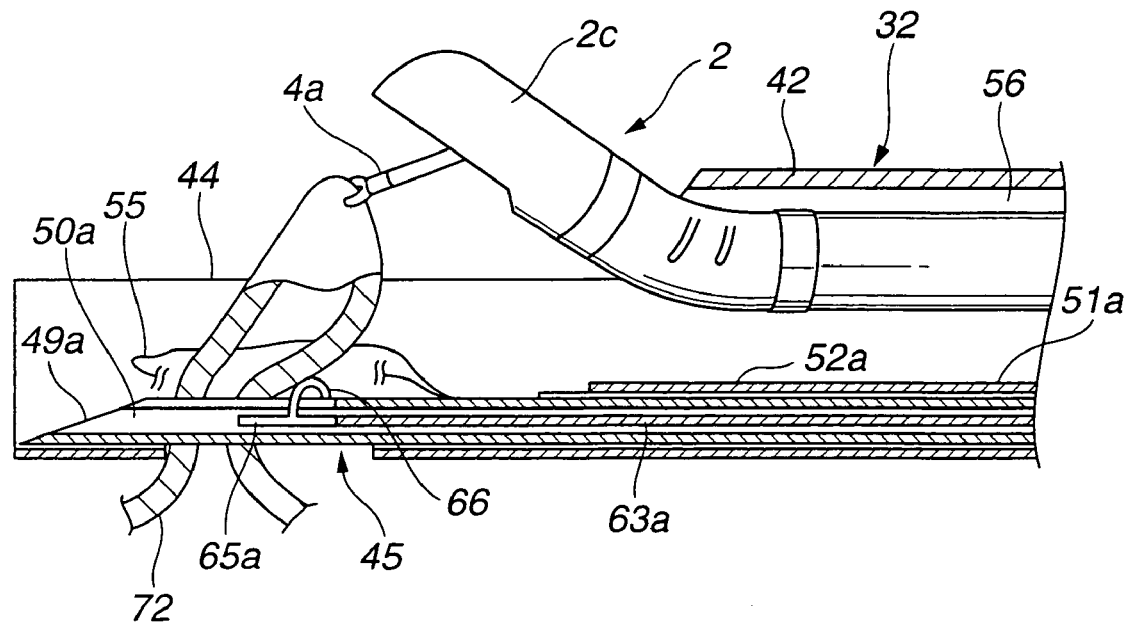
FIG. 20 is an explanatory diagram showing clamping and lifting of an intended region performed using the endoscopic treatment system shown in FIG. 12.
Figure 21:
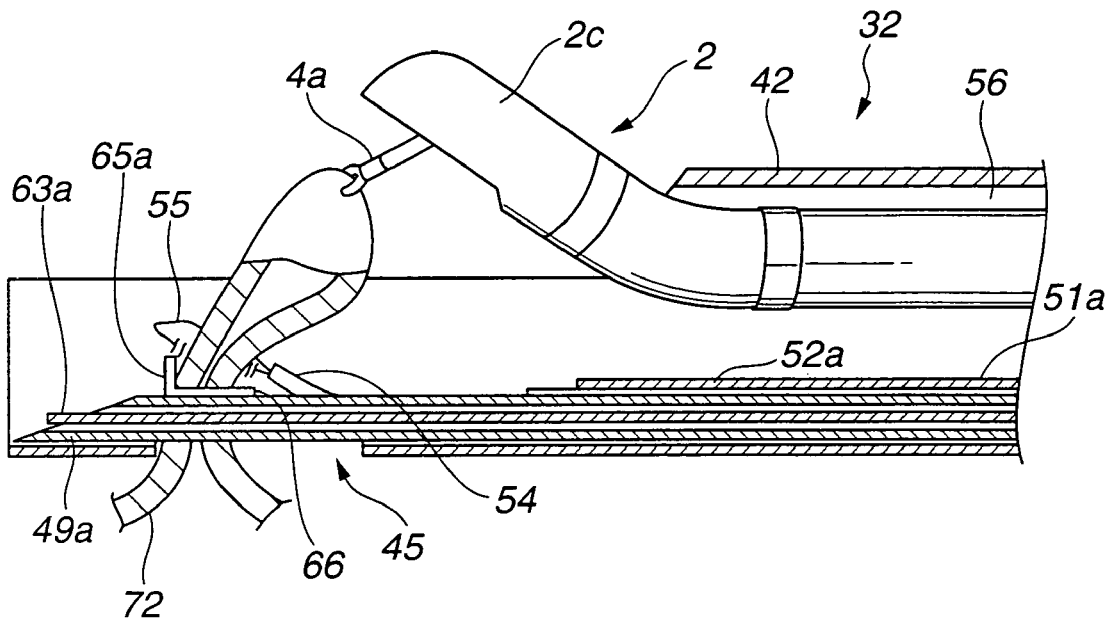
FIG. 21 is an explanatory diagram showing ligation and resection of an intended region performed using the endoscopic treatment system shown in FIG. 12.
Figure 22:
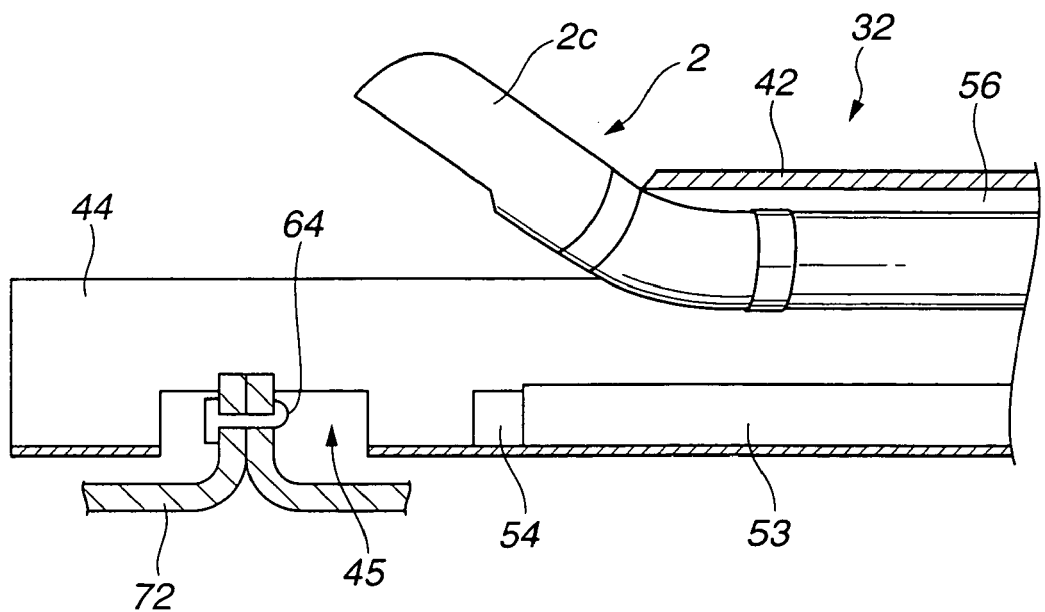
FIG. 22 is an explanatory diagram showing a movement made after the completion of ligation and resection performed using the endoscopic treatment system shown in FIG. 12.

The system insertion aid 33 is mounted on the outer surface of a large intestinal endoscope 71, and inserted into near an intended region in the large intestine 72, for example, near the cecum 70 (see FIG. 17). The large intestinal endoscope 71 is then removed from the system insertion aid 33. The endoscope 2 passed through the therapeutic instruments insertion aid 32 is inserted into the system insertion aid 33 on behalf of the large intestinal endoscope 71 (see FIG. 18).

Consequently, the endoscope 2 passed through the therapeutic instruments insertion aid 32 is inserted into the system insertion aid 33 that has been inserted to near the cecum 70 that is the intended region in the large intestine 72. Thereafter, the endoscope 2 (an observation device that serves as an observing means included in the distal section 2c of the endoscope 2, and that is formed with an electronic image pickup device or the like) is used to observe the intended region through the lateral hole 45 of the sheath 42 of the therapeutic instruments insertion aid 32. The inserted position of the sheath 42 of the therapeutic instruments insertion aid 32 is adjusted such that the center of the lateral hole 45 will be aligned with the center of the intended region (see FIG. 19).

When the intended region in the large intestine 72 can be observed through the lateral hole 45 of the sheath 42 included in the therapeutic instruments insertion aid 32, the distal damper 4a of the pair of clamp forceps 4 lying through the endoscope 2 is projected to the lateral hole 45 in order to clamp the intended region in the large intestine 72. Moreover, the distal section 2c of the insertion unit 2a is raised in order to lift the intended region in the large intestine 72 through the lateral hole 45. The large intestine 72 clamped with the distal damper 4a and lifted through the lateral hole 45 with the raising of the distal section 2c is constricted by tightening of the loop wire 55 disposed to encircle the lateral hole 45. With the large intestine 72 constricted with the loop wire 55, the needle sheaths 61a and 61b (see FIG. 12) are pushed into the needle sliders 35a and 35b respectively. The puncturing needles 49a and 49b pierce all the layers of the large intestine 72 (see FIG. 20).

Thereafter, the pusher wire stoppers 48a and 48b are handled in order to thrust the pusher wires 60a and 60b. Consequently, the ligature unit 64 is thrust out of the puncturing needles 49a and 49b by means of the ligature unit pushers 63a and 63b. Eventually, all the layers of the large intestine 72 are sandwiched between the T bars 65a and 65b and the T bar sheath 66 and thus ligated (see FIG. 21).

After the large intestine 72 is thus ligated with the ligature unit 64, the puncturing needles 49a and 49b are pulled out of the large intestine 72. While the loop wire 55 is further tightened, a high-frequency current is conducted to the metallic loop wire 55 in order to resect the large intestine 72. After the large intestine 72 is resected, the metallic loop wire 55 and puncturing needles 49a and 49b are removed. Consequently, the large intestine 72 is ligated with the ligature unit 64 in the resected portion thereof (see FIG. 22).

Using the endoscopic treatment system 31 of the second embodiment, the therapeutic instruments insertion aid and endoscope can be reliably inserted into the deep region in the large intestine. Moreover, although the staple type ligatures 18 employed in the endoscopic treatment system 1 of the first embodiment cannot be collected after completion of a cure, the ligature 64 employed in the second embodiment can be collected by cutting the sheath 65 linking the T bars 65a and 65b.

Incidentally, the metallic loop wire 55 disposed to encircle the lateral hole 45 formed in the distal part of the sheath 42 included in the therapeutic instruments insertion aid 32 is fixed to encircle the lateral hole 45 such that it can be freely unlocked. Thus, the root of a lifted portion of the large intestine can be constricted reliably. Unless the loop of the metallic loop wire 55 is locked, the loop is pushed up by the lifted large intestine. It becomes hard to enclose the root of the lifted portion of the large intestine with the loop.

Figure 23:
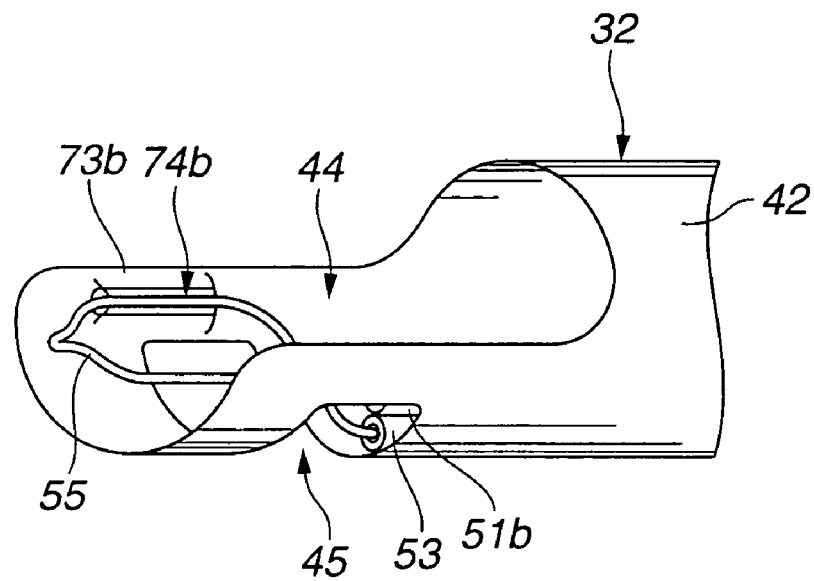
FIG. 23 is a perspective view showing a resecting metallic loop disposed in the distal part of the therapeutic instruments insertion aid shown in FIG. 13.
Figure 24:
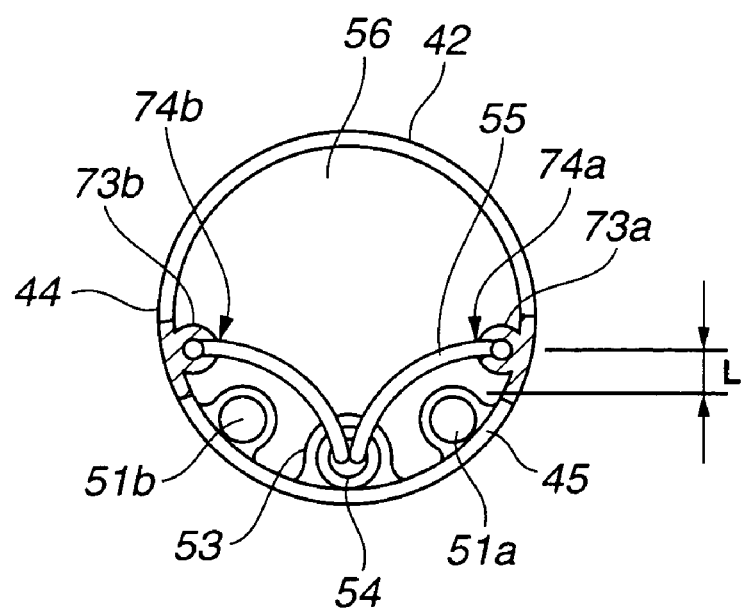
FIG. 24 is a sectional view showing a cutting plane of the distal part of the therapeutic instruments insertion aid shown in FIG. 13 which is orthogonal to the axial direction of an endoscope passage channel.

Therefore, metallic wire locking members 73a and 73b having substantially the same length as the lateral hole 45 may be, as shown in FIG. 23 and FIG. 24, formed as integral parts of the sheath 42 on the internal surface of the sheath 42 such that metallic wire locking members will extend substantially parallel to the lateral hole 45 in the longitudinal-axis direction of the sheath 42.

The metallic wire locking members 73a and 73b have slits 74a and 74b respectively whose inner diameter is substantially equal to the outer diameter of the metallic loop wire 55 and whose width is smaller than the outer diameter of the metallic loop wire 55. Moreover, the metallic wire locking members 73a and 73b are located nearer to the slit 44 by a dimension L than the puncturing needle channels 51a and 51b are.

The loop of the metallic loop wire 55 is fitted and locked in the metallic wire locking members 73a and 73b. When the large intestine 72 is lifted through the lateral hole 45 by moving the endoscope 2, the metallic loop wire 55 locked in the metallic wire locking members 73a and 73b is disposed at the root of the lifted portion of the large intestine 72. The puncturing needles are pierced into all the layers of the root of the lifted portion of the large intestine 72. Thereafter, when the metallic loop wire 55 is tightened, the loop comes off the metallic wire locking members 73a and 73b. Consequently, the large intestine is constricted at a position separated by the dimension L from the puncturing needles piercing the root of the lifted tissue of the large intestine 72.

As mentioned above, the positional relationship between the puncturing needles that serve as ligating means and the metallic loop wire that serves as resecting means is held constant. An intended region can be reliably resected with a margin left. Incidentally, the method of locking the metallic wire is not limited to the aforesaid one as long as the metallic wire can be temporarily locked in order to constrict a living-body tissue, which is lifted with a pair of clamp forceps lying through an endoscope, at a right position.

Next, an endoscopic treatment system in accordance with a third embodiment of the present invention will be described in conjunction with FIG. 25 to FIG. 29.

Figure 25:
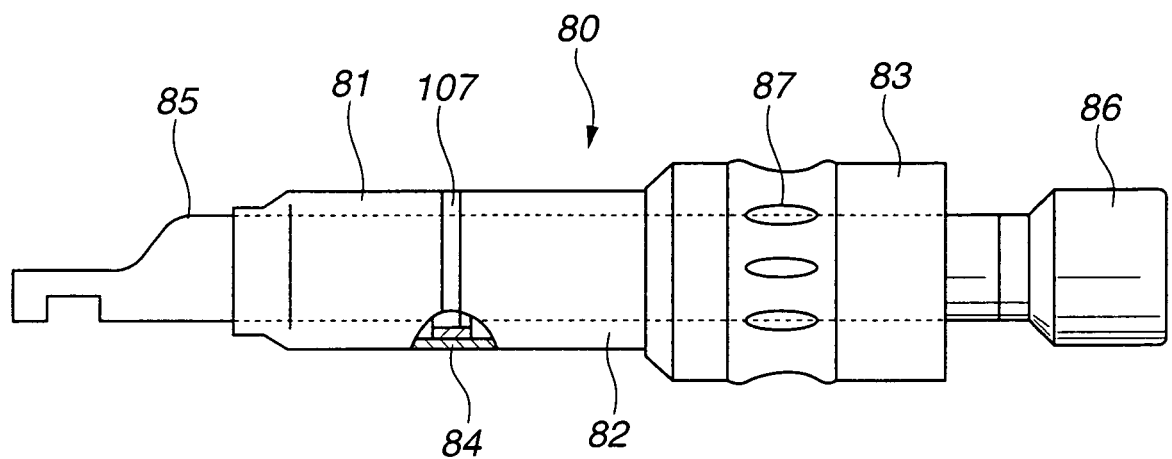
FIG. 25 is a plan view showing the structure of a system insertion aid included in an endoscopic treatment system in accordance with a third embodiment of the present invention.

In the third embodiment of the endoscopic treatment system, a system insertion aid 80 mounted on the outer surface of an endoscope comprises, as shown in FIG. 25, a distal sheath 81, an operator-side sheath 82, and a grip 83 formed at the proximal end of the operator-side sheath 82. The distal sheath 81 and operator-side sheath 82 are coupled to each other with a coupling member 84 between them. The grip 83 has a hardness variation knob 87.

A sheath 85 of a therapeutic instruments insertion aid 86 to be mounted on the outer surface of the endoscope is passed through the system insertion aid 80. The sheath 85 of the therapeutic instruments insertion aid 86 is jutted out of the distal end of the distal sheath 81 of the system insertion aid 80 such that the sheath 85 can freely slide. The clearance between the sheath 85 and distal sheath 81 is narrowed to be substantially zero or ranges from about 1 mm to about 3 mm.

The therapeutic instruments insertion aid 86 has the same shape and ability as the therapeutic instruments insertion aids 3 and 32 employed in the first and second embodiments.

The distal sheath 81 and operator-side sheath 82 included in the system insertion aid 80 are made of a relatively soft resin material, for example, polyurethane, vinyl chloride, polyurethane elastomer, polystyrene elastomer, polyolefin elastomer, polyester elastomer, polyamide elastomer, (porous) fluorocarbon resin, or any other thermoplastic elastomer. The length of the distal sheath 81 is substantially the same as the sum of the lengths of the transverse colon and ascending colon. Moreover, the length of the operator-side sheath 82 is substantially the same as the length of the descending colon.

Figure 26:
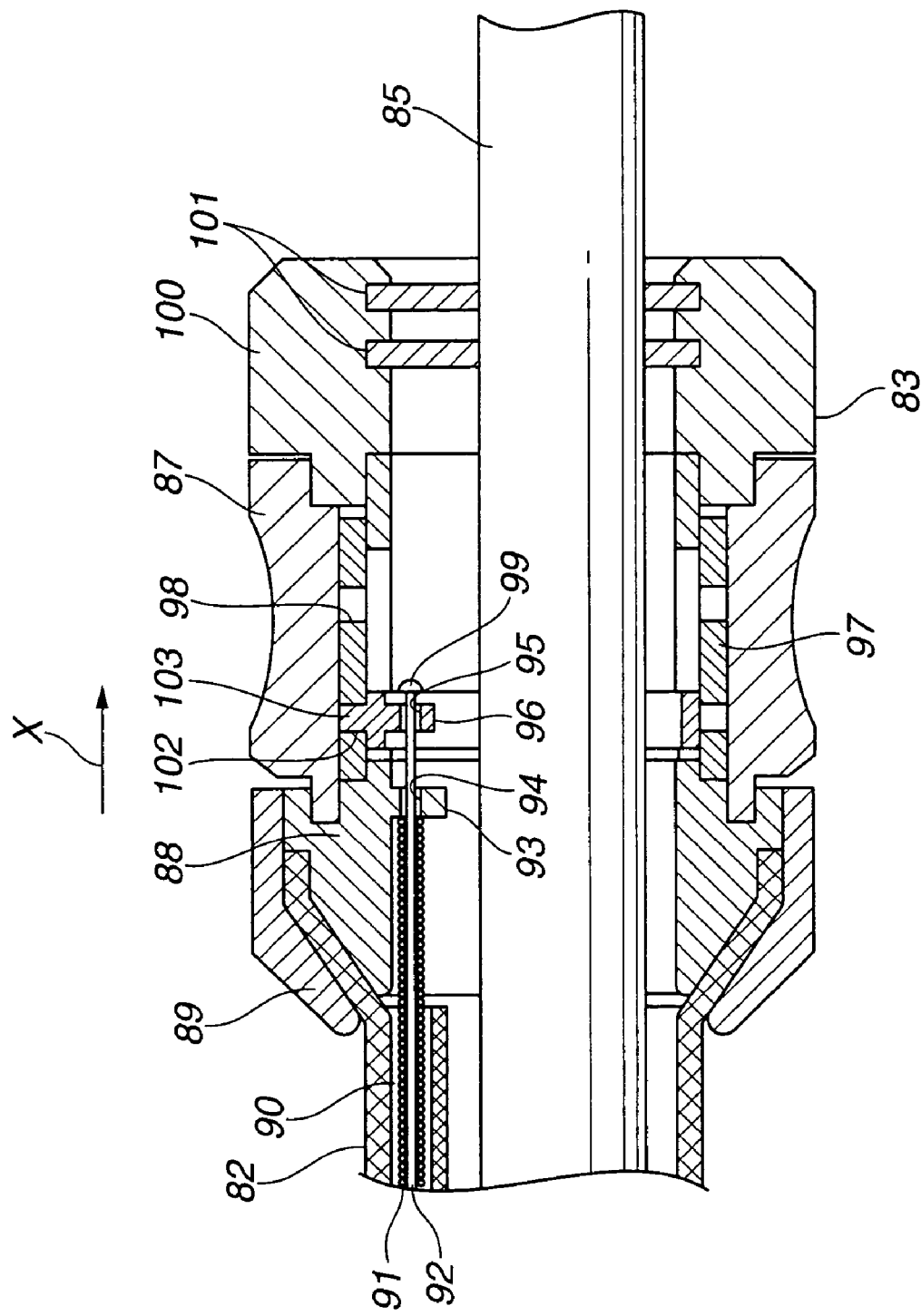
FIG. 26 is a sectional view showing an operator-side sheath and a damper included in the system insertion aid shown in FIG. 25.

The proximal end of the operator-side sheath 82 included in the system insertion aid 80 is fixed to the grip 83. The operator-side sheath 82 and grip 83 are secured, as shown in FIG. 26, owing to a grip body 88 that is provided to the distal part of the grip 83 and that has a conical part with which the proximal end of the operator-side sheath 82 is engaged, and a lock screw 89 that has a female screw thereof meshed with a male screw threaded on the outer surface of the grip body 88 and that has a slope which clamps the operator-side sheath 82 engaged with the conical part of the grip body 88.

A hardness variation member passage channel 90 is formed inside the internal surface of the operator-side sheath 82 from the proximal end of the operator-side sheath 82 to the distal end thereof in the longitudinal-axis direction thereof.

A compression coil 91 and a traction wire 92 enclosed in the compression coil are run through the hardness variation member passage channel 90. The proximal end of the compression coil 91 is brazed and fixed to a compression coil locking member 93 formed on the internal surface of the grip body 88 substantially concentrically with the hardness variation member passage channel 90. The proximal end of the traction wire 92 enclosed in the compression coil 91 is fixed to a stopper 99 after being passed through a traction wire passage hole 94 formed in the compression coil locking member 93 and a traction wire passage hole 95 formed in a movable member 96.

The movable member 96 having the traction wire passage hole 95 through which the traction wire 92 is passed is formed with a ring shaped member. A traction wire receptor 102 having the traction wire passage hole 95 is formed inside the variable member 96. A cam member 97 being substantially cylindrical and having a spiral cam groove 98 formed in the lateral side thereof is disposed outside the movable member 96. A guide 103 is fitted in the cam groove 98 such that it can freely slide.

The cam member 97 is fixed to the hardness variation knob 87. When the hardness variation knob 87 is turned, the cam member 97 is rotated. This cases the traction wire 92 to slide in the axial direction of the operator-side sheath 82 towards the operator side of the operator-side sheath.

On the operator side of the hardness variation knob 87, a pressing member 100 is fixed to the grip body 88. The pressing member 100 has valves 101, whereby the space around the sheath 85 of the therapeutic instruments insertion aid is kept watertight and airtight.

Figure 27:
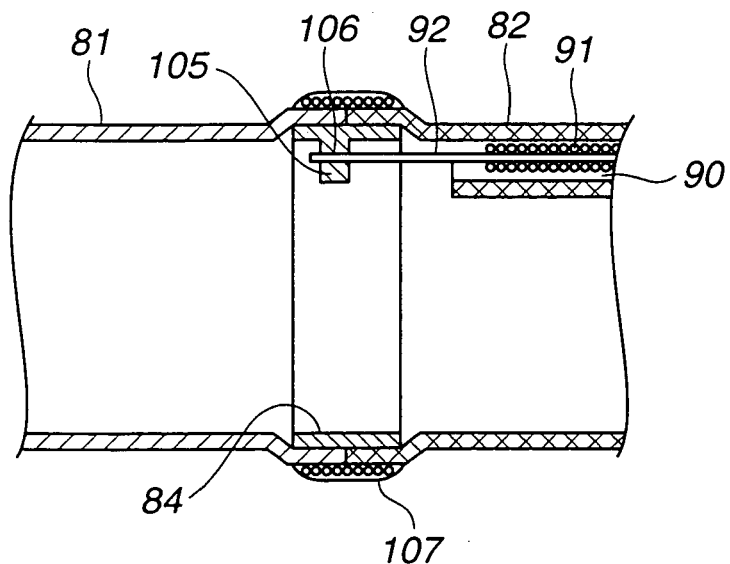
FIG. 27 is a sectional view showing a joint between the distal sheath and operator-side sheath included in the system insertion aid shown in FIG. 25.

The distal end of the operator-side sheath 82 and the proximal end of the distal sheath 81 are, as shown in FIG. 27, engaged with the coupling member 84. A thread is wound about the peripheries of the operator-side sheath 82 and distal sheath 81, which are engaged with the coupling member 84, and an adhesive 107 is applied to the thread for fixation.

The inner diameter of the coupling member 84 is substantially identical to the inner diameter of the distal sheath 81 and operator-side sheath 82. A traction wire locking member 105 is formed as part of the internal surface of the coupling member 84 and has substantially the same height as the hardness variation member passage channel 90.

The traction wire locking member 105 is substantially concentric to the hardness variation member passage channel 90, and has a traction wire locking hole 106 bored along the same axis as the center axis of the hardness variation member passage channel 90. The distal end of the traction wire 92 lying through the hardness variation member passage channel 90 is inserted into the traction wire locking hole 106 and brazed for fixation.

The distal end of the compression coil 91 is brazed and fixed to the traction wire 92 within the distal part of the hardness variation member passage channel 90 lying through the operator-side sheath 82.

Specifically, when the hardness variation knob 87 of the grip 83 is turned, the cam member 97 is driven. This causes the traction wire 92 to slide or be led into the proximal side of the operator-side sheath 82. When the traction wire 92 slides, the compression coil 91 contracts. The operator-side sheath 82 is hardened. When the hardness variation knob 87 is turned, the traction wire 92 is thrust forward to the distal side of the operator-side sheath 82. Consequently, the compression coil 91 slackens and the operator-side sheath 82 becomes flexible.

Treating the large intestine 109 using the endoscopic treatment system including the system insertion aid 80 having the foregoing structure will be described in conjunction with FIG. 28 and FIG. 29.

Figure 28:
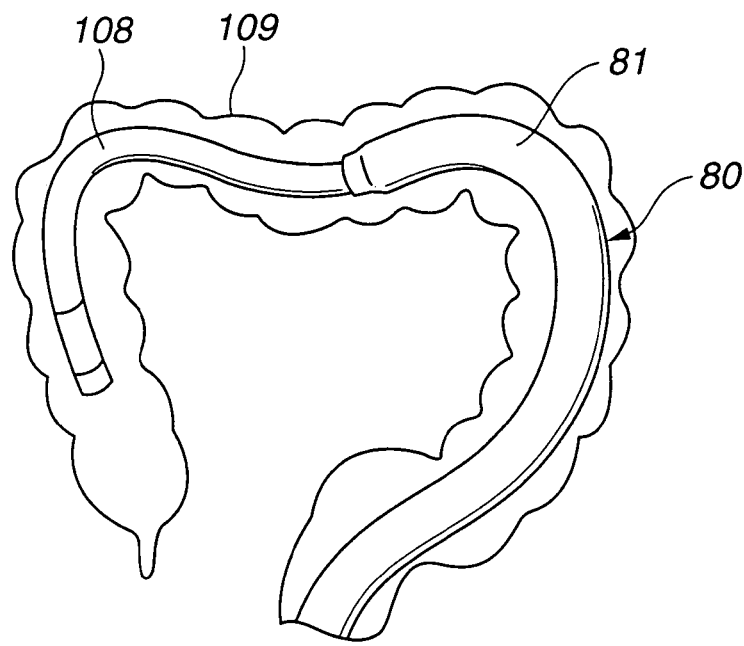
FIG. 28 is an explanatory diagram showing the operation during treatment of the large intestine performed using the endoscopic treatment system shown in FIG. 25.
Figure 29:
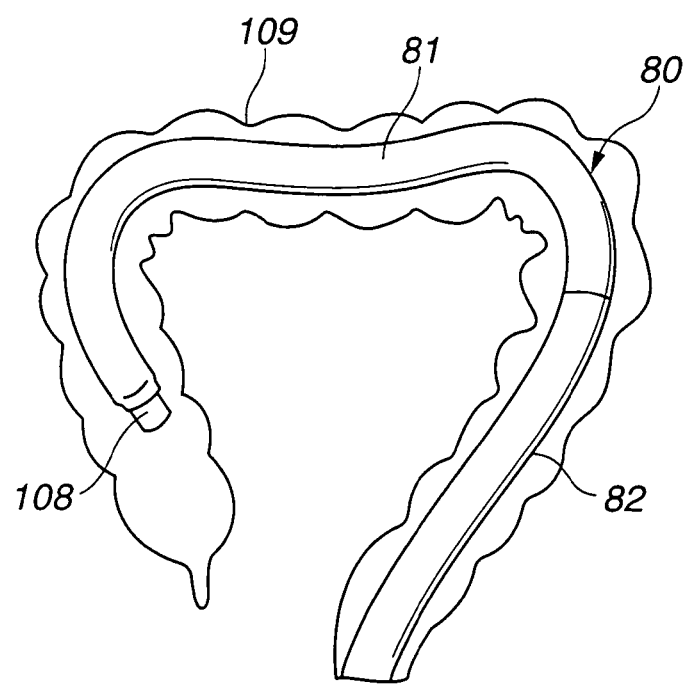
FIG. 29 is an explanatory diagram showing the operation during treatment of the large intestine performed using the endoscopic treatment system shown in FIG. 25.

As shown in FIG. 28, the distal sheath 81 of the system insertion aid 80 is advanced along the outer surface of the endoscope 108 that is inserted into the large intestine 109 beforehand. When the distal sheath 81 of the system insertion aid 80 advanced along the outer surface of the endoscope 108 reaches near the middle of the transverse colon, the system insertion aid 80 may not be able to be inserted farther because of the softness of the operator-side sheath 82. In this case, the hardness variation knob 87 included in the grip 83 is turned. The cam member 97 rotates with the turn of the hardness variation knob 87. The guide 103 fitted in the cam groove 98, that is, the movable member 96 moves in the direction of arrow X in FIG. 26. The stopper 99 of the traction wire 91 is abutted on the variable member 96. Consequently, the traction wire 92 is moved in the same direction in FIG. 26.

Along with the movement of the traction wire 92, the compression coil 91 fixed to the distal part of the traction wire 92 moves in the same direction. Since the compression coil is locked in the compression coil locking member 93, the compression coil 91 receives strong compressive stress and becomes hard.

Owing to the traction wire 92 and compression coil 91, the operator-side sheath 82 becomes hard and straightens up as a whole. The distal sheath 51 maintains flexibility. Consequently, the system insertion aid 80 can be, as shown in FIG. 29, easily inserted into the deep region in the large intestine 109.

The inclusion of the hardness variation mechanism in the system insertion aid 80 improves the maneuverability in inserting the system insertion aid to the deep region in the large intestine.

According to the third embodiment, the maneuverability in insertion is improved with the inclusion of the hardness variation mechanism in the operator-side sheath. A method of ensuring the maneuverability in insertion is not limited to the inclusion of the hardness variation mechanism. Alternatively, for example, an inserting section of a system insertion aid is formed as a united body, a forceps passage channel is formed to extend from the distal end of the inserting section to the operator-side end thereof, and a metallic wire or the like is inserted into the forceps passage channel through a forceps port of the forceps passage channel formed in the operator side of the system insertion aid or in a grip thereof. Thus, the hardness of a portion of the inserting section having any length from the operator-side end thereof may be varied. Otherwise, the distal sheath may be made of a high-flexibility soft resin, and the operator-side sheath may be made of a low-flexibility hard resin, so that the maneuverability in insertion may thus be ensured.

Next, an endoscopic treatment system in accordance with a fourth embodiment of the present invention will be described in conjunction with FIG. 30 to FIG. 32.

Figure 30:
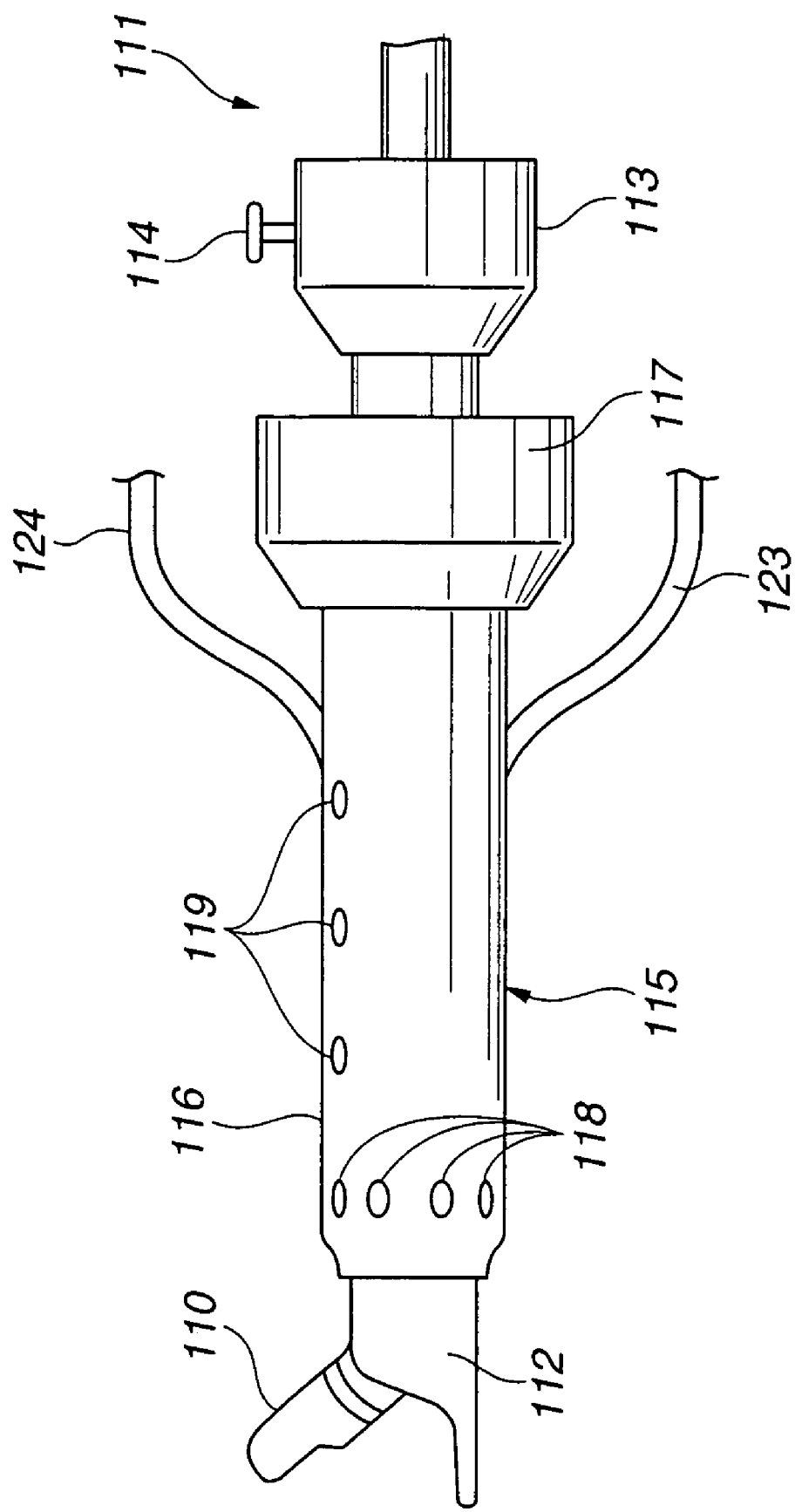
FIG. 30 is a plan view showing a system insertion aid employed in an endoscopic treatment system in accordance with a fourth embodiment of the present invention.

The endoscopic treatment system in accordance with the fourth embodiment comprises, as shown in FIG. 30, an endoscope 110, a therapeutic instruments insertion aid 111 into which the endoscope 110 is inserted, and a system insertion aid 115 into which the therapeutic instruments insertion aid 111 mounted on the outer surface of the endoscope 110 is inserted.

The therapeutic instruments insertion aid 111 comprises a sheath 112 through which the insertion unit of the endoscope 110 is passed, and a grip 113 formed at the proximal end of the sheath 112. The grip 113 has an endoscope locking member 114.

The system insertion aid 115 comprises a sheath 116 through which the sheath 112 of the therapeutic instruments insertion aid 111 is passed, and a grip 117. Moreover, the system insertion aid 115 comprises: a plurality of suction holes 118 bored circumferentially in the periphery of the distal part of the sheath 116; a plurality of air outlets 119 bored in a lateral side of the sheath 116 in the longitudinal-axis direction thereof; and a suction tube 123 and an exhaust tube 124 extended from the operator side of the sheath 116.

Figure 31:
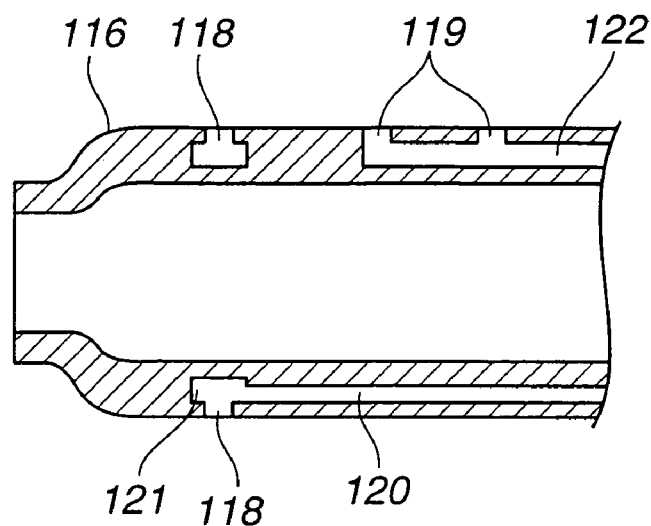
FIG. 31 is a sectional view of the distal part of the system insertion aid shown in FIG. 30.

The plurality of suction holes 118 bored circumferentially in the distal part of the sheath 116 of the system insertion aid 115 communicate with a suction chamber 121 as shown in FIG. 31. The suction chamber 121 communicates with the suction tube 123 (see FIG. 30) via a suction channel 120. The suction tube 123 is led to a sucking/pressurization pump that is not shown.

Moreover, the plurality of air outlets 119 are bored in one lateral side of the sheath 116 in the longitudinal-axis direction thereof. The air outlets 119 communicate with, as shown in FIG. 31, the exhaust tube 124 (see FIG. 30) via an exhaust channel 122 extended from the distal end of the sheath 116 to the operator-side end thereof. The proximal end of the exhaust tube 124 communicates with the atmosphere via a release valve that can be freely closed or opened.

Figure 32:
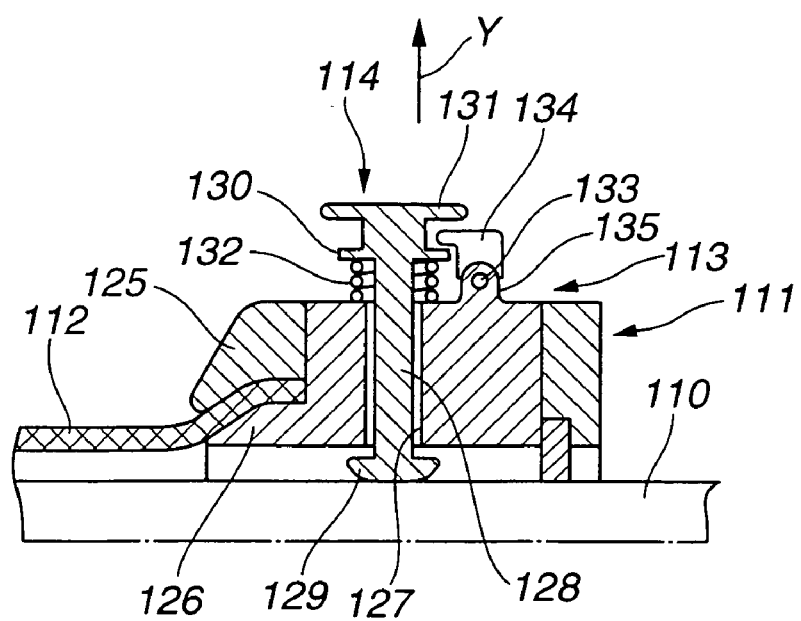
FIG. 32 is a sectional view showing an endoscope locking member included in the system insertion aid shown in FIG. 30.

The grip 113 of the therapeutic instruments insertion aid 111 includes, as shown in FIG. 32, a grip body 126 that holds or locks the proximal part of the sheath 112, and a lock screw 125. The grip body 126 has a substantially cylindrical shape as a whole, includes a substantially conical section with which the sheath 112 is engaged. When the proximal part of the sheath 112 is engaged with or mounted on the conical section, the lock screw 125 is tightened.

The grip body 126 has a locking member channel 127, through which the inside of the grip body and the outside thereof communicate with each other. The endoscope locking member 114 is mounted freely slidably on the locking member channel 127.

The endoscope locking member 114 comprises: a locking member sheath 128 mounted freely slidably on the locking member channel 127; an endoscope insertion unit presser 129 that is extended to the endoscope passage channel inside the sheath 112; a substantially disk-like spring presser 130 that secures a pressing spring 132, which forces the locking member sheath 128 to move toward the endoscope passage channel, between the spring presser and grip body 126; and a button 131 formed externally to the spring presser 130 and used to press down the locking member sheath 128 against the pressing spring 132. Namely, the endoscope locking member 114 has the locking member sheath 128 constrained to move in the direction of arrow Y in FIG. 32 by means of the pressing spring 132 interposed between the periphery of the grip body 126 and spring presser 130.

Furthermore, when the button 131 of the endoscope locking member 114 is pressed down against the pressing spring 132, the insertion unit of the inserted endoscope 110 is held and locked with the endoscope insertion unit presser 129 formed at the distal end of the locking member sheath 128.

At this time, a button presser 134 of which one end is pivoted on a shaft 133 borne by a bearing 135 located near the locking member sheath 128 of the grip body 126 and which has a hook-like projection is abutted on the upper surface of the spring presser 130 included in the endoscope locking member 114. Thus, the locked and hold state of the endoscope attained by the endoscope locking member 114 can be maintained.

Incidentally, the endoscope insertion unit presser 129 abutted on the insertion unit of the endoscope 110 is formed with a substantially soft elastic member made of, for example, a silicon rubber or polyurethane rubber. An anti-sliding groove should be formed in the surface of the endoscope insertion unit presser 129 that is brought into contact with the insertion unit of the endoscope 110.

Treating the large intestine using the system insertion aid 115 will be described in conjunction with FIG. 33 and FIG. 34.

Figure 33:
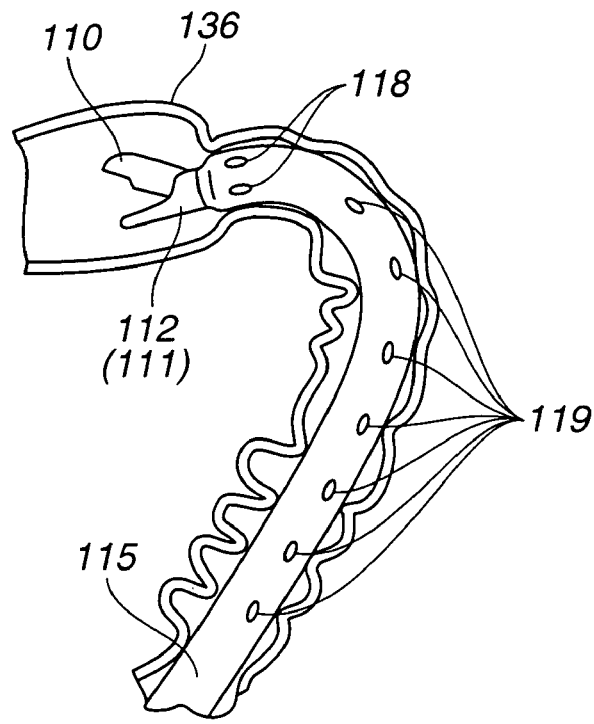
FIG. 33 is an explanatory diagram showing the operation during treatment of the large intestine performed using the endoscopic treatment system shown in FIG. 30.

As shown in FIG. 33, the sheath 112 of the therapeutic instruments insertion aid 111 is mounted on the outer surface of the endoscope 110, and the system insertion aid 115 is mounted on the outer surface of the sheath 112 of the therapeutic instruments insertion aid. In this state, the system insertion aid 115 is inserted into the transverse colon of the large intestine 136.

After the system insertion aid 115 is thus inserted into an intended region in the large intestine 136, a suction pump that is not shown is used to perform suction through the suction holes 118. Consequently, the large intestine 136 is sucked and fixed to the distal end of the system insertion aid 115. The positional relationship between the distal end of the system insertion aid 115 and the large intestine 136 is nearly fixed.

In this state, the large intestine 136 and the distal end of the system insertion aid 115 are brought into close contact with each other. Therefore, even when the endoscope 110 performs aeration, no air will be sucked through the suction holes 118. The portion of the large intestine spread at the distal side of the system insertion aid 115 is dilated with the air supplied from the endoscope 110, whereby a working space is created.

In this state, excessive air is released from the lumen of the large intestine 136 through the air outlets 119 bored along the sheath 115 of the system insertion aid 115. This causes the large intestine to slacken and wrinkle appropriately. Consequently, the system insertion aid 115 can be unforcedly advanced along the internal wall of the large intestine 136.

After the positional relationship between the large intestine 136 and the distal end of the system insertion aid 115 is thus fixed, the therapeutic instruments insertion aid 112 and endoscope 110 are used to treat the intended region.

Figure 34:
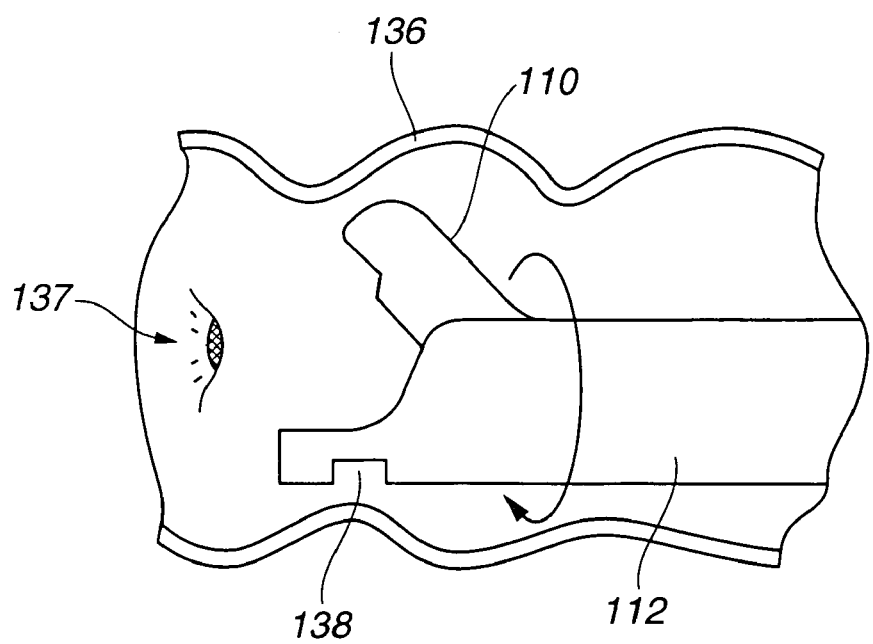
FIG. 34 is an explanatory diagram showing insertion into an intended region in the large intestine performed using the endoscopic treatment system shown in FIG. 30.

In order to lift, ligate, and resect the intended region 137 in the large intestine 136 as shown in FIG. 34, the therapeutic instruments insertion aid 112 must be moved such that the lateral hole 138 of the therapeutic instruments insertion aid 112 will be aligned with the intended region 137. The lateral hole 138 of the therapeutic instruments insertion aid 112 is aligned with the intended region 137 with the endoscope 110 mounted and locked to the therapeutic instruments insertion aid 112.

In order to lock the endoscope 110 in the therapeutic instruments insertion aid 112, after the endoscope 110 is inserted into the therapeutic instruments insertion aid 112, the endoscope locking member 114 included in the therapeutic instruments insertion aid 112 is pressed down against the pressing spring 132. Consequently, the endoscope insertion unit presser 129 included in the endoscope locking member 114 abuts on the insertion unit of the endoscope 110. Moreover, the spring presser 130 is hooked with the hook-like portion of the button pressing member 134, and the endoscope locking member 114 is immobilized. Consequently, both the endoscope 110 and therapeutic instruments insertion aid 113 are locked.

As mentioned above, when the therapeutic instruments insertion aid 112 is aligned with the intended region 137, both the endoscope 110 and therapeutic instruments insertion aid 113 are locked using the endoscope locking member 114. Otherwise, the endoscope locking member 114 may be freed, and the endoscope 110 and therapeutic instruments insertion aid 113 may be moved mutually freely in order to treat the intended region 137.

Since the endoscope treatment system employs the foregoing system insertion aid, the positional relationship between the intended region in the large intestine or the like and the treatment system can be held constant. Therefore, the intended region will not be lost during treatment. Moreover, since the inserting section of the system insertion aid has the air outlets, excessive air can be released from the large intestine and a load imposed on the large intestine, such as, excessive stretch of the large intestine due to air can be alleviated. Furthermore, since the means for locking both the therapeutic instruments insertion aid and endoscope is included, the relative positions thereof will not change during treatment. This leads to improved precision in treatment. Furthermore, the inserting section of the therapeutic instruments insertion aid and the insertion unit of the endoscope can be twisted simultaneously. Thus, the ability to follow a twist improves.

Figure 35:
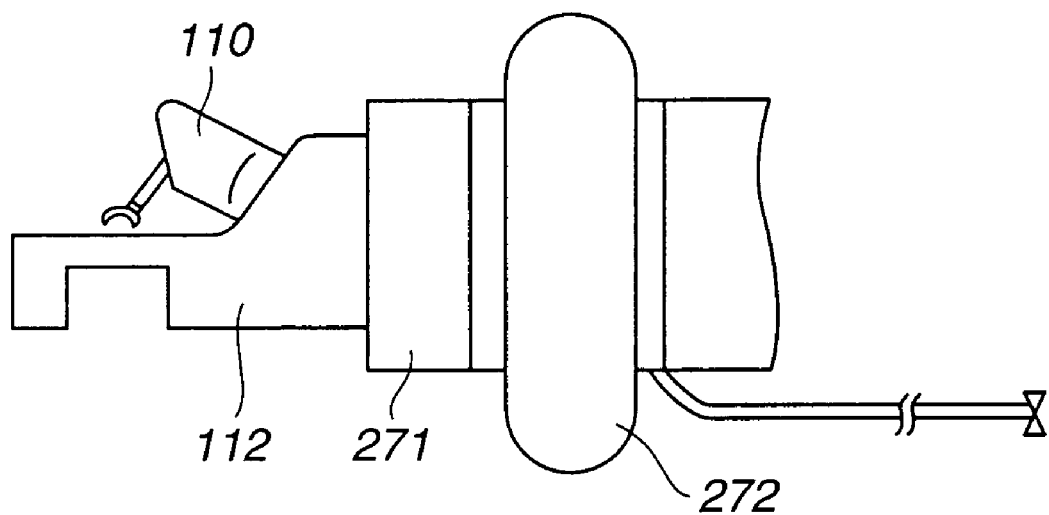
FIG. 35 is a plan view showing other form of the system insertion aid shown in FIG. 30.

As a method of locking the system insertion aid in a body cavity such as the large intestine, like other embodiment shown in FIG. 35, a balloon 272 may be mounted on the distal part of a system insertion aid 271. By dilating the balloon 272, the system insertion aid 271 can be locked at a predetermined position in the body cavity such as the large intestine.

Next, a therapeutic instruments insertion aid employed in an endoscopic treatment system in accordance with a fifth embodiment of the present invention will be described in conjunction with FIG. 36 and FIG. 37.

The therapeutic instruments insertion aid 140 employed in the fifth embodiment of the present invention comprises an endoscope passage channel 141 extended from the distal end of the therapeutic instruments insertion aid to the operator-side end thereof, a cutter passage channel 142, and puncturing needle passage channels 143. Moreover, the therapeutic instruments insertion aid 140 comprises: a hard tissue retainer 144 that is a thin plate formed substantially like a semicircular member laid along the external surface of the distal end; hard bar-like retainer arm members 145 connected to both the ends of the tissue retainer 144 and capable of advance or withdraw parallel to each other in the longitudinal-axis direction of the therapeutic instruments insertion aid 140 on the outer surface of the therapeutic instruments insertion aid; retainer sliders 146 that enclose the respective retainer arm members 145 and are formed parallel to each other in the longitudinal-axis direction of the therapeutic instruments insertion aid 140 on the outer surface of the therapeutic instruments insertion aid; connection tubes 147 connected to the proximal ends of the respective retainer sliders 146 and extended to the operator side of the therapeutic instruments insertion aid; and metallic wires 148 coupled to the proximal ends of the respective retainer arm members 145 and extended to the operator side of the therapeutic instruments insertion aid through the channels of the respective connection tubes 147.

A handle member that is not shown and used to advance or withdraw the metallic wires 148 and connection tubes 147 is coupled to the proximal ends of the connection tubes 147. Incidentally, the puncturing needle passage channels 143 are located on the opposite position of the endoscope passage channel 141 with the cutter passage channel 142 between them, though one of the puncturing needle passage channels 143 is not shown in FIG. 36. The puncturing needle passage channels are disposed substantially parallel to each other within the endoscope passage channel 141.

Figure 36:
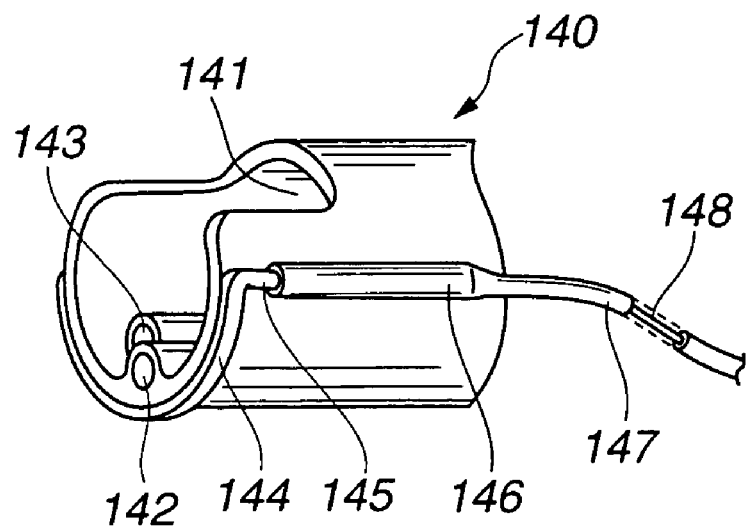
FIG. 36 is a perspective view showing the structure of a therapeutic instruments insertion aid employed in an endoscopic treatment system in accordance with a fifth embodiment of the present invention.
Figure 37:
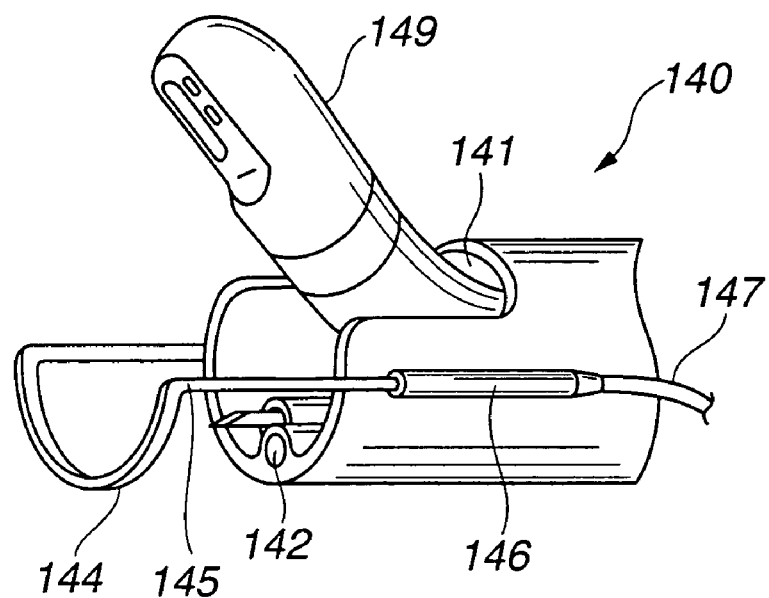
FIG. 37 is a perspective view showing an operation state of an endoscope that is passed through the therapeutic instruments insertion aid shown in FIG. 36.

When the therapeutic instruments insertion aid 140 having the foregoing structure is inserted into the large intestine or into a system insertion aid, the tissue retaining member 144 has, as shown in FIG. 36, the retainer arm members 145 accommodated in the respective retainer sliders 146. After the therapeutic instruments insertion aid reaches an intended region in the large intestine, the handle member is handled in order to thrust the metallic wires 148. This causes the retainer arm members 145 to extend from the respective retainer sliders 146 and jut out of the distal end of the therapeutic instruments insertion aid 140. Consequently, the tissue retaining member 144 is projected from the distal end of the therapeutic instruments insertion aid 140. With the tissue retaining member 144 jutted out of the distal end of the therapeutic instruments insertion aid 140, the intended region in the large intestine is observed using the endoscope 149 passed through the endoscope passage channel 141. Meanwhile, the intended region is clamped and lifted using a pair of clamp forceps, which is not shown and lies through the endoscope 149, within a space defined by the tissue retaining member 144, retainer arm members 145, and distal end of the therapeutic instruments insertion aid 140. The clamped and lifted intended region in the large intestine has all the layers thereof ligated and resected in the same manner as described in relation to the second to fourth embodiments.

Unlike the therapeutic instruments insertion aids included in the second to fourth embodiment, the distal end of the therapeutic instruments insertion aid 140 has no lateral hole. Consequently, the length of a hard distal part of the therapeutic instruments insertion aid is shortened. This leads to the improved ease of inserting the therapeutic instruments insertion aid. Moreover, the size of a portion of the large intestine to be clamped and lifted can be changed by adjusting a degree of projection by which the tissue retaining member is projected. Consequently, the size of a tissue to be resected can be adjusted.

Figure 38:
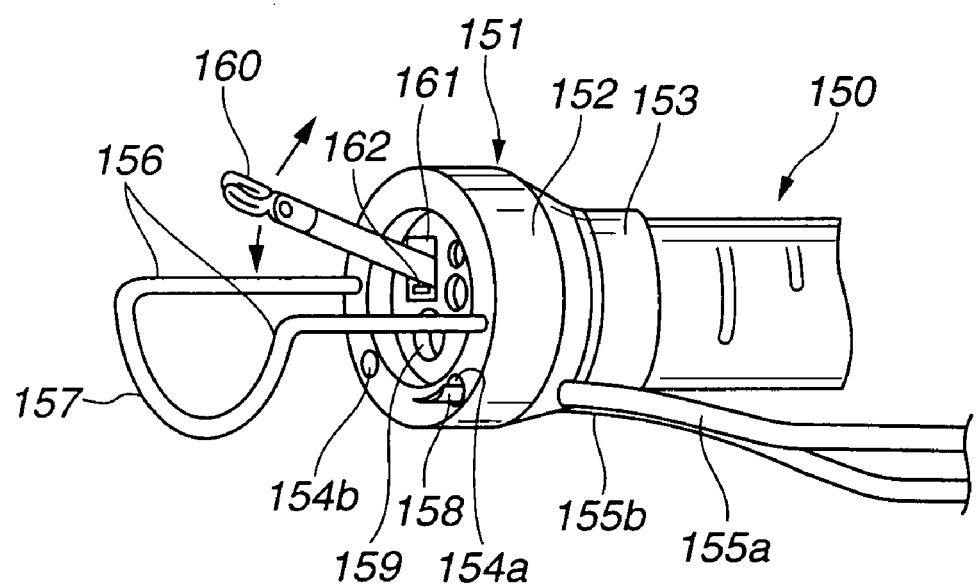
FIG. 38 is a perspective view showing the structure of a variant of the therapeutic instruments insertion aid shown in FIG. 36.

Next, a variant of the fifth embodiment will be described in conjunction with FIG. 38, FIG. 39, and FIG. 40. This variant is an endoscopic treatment system in which a tissue retaining member and puncturing needle passage channels can be externally attached to an endoscope.

To begin with, a description will be made of an endoscopic treatment system having a freely detachable treatment cap 151 attached to the distal end of a substantially cylindrical endoscope 150. The treatment cap 151 comprises: a treatment cap body 152 which is shaped cylindrically, whose inner diameter is a little larger than the maximum diameter of the distal part of the cylindrical endoscope 150, and which is made of a hard and transparent resin material; and a treatment cap attachment member 153 which is continuously connected to one end of the treatment cap body 152, whose inner diameter is a little smaller than the outer diameter of the distal part of the endoscope 150, and which is made of an elastic material such as a silicon rubber or fluorocarbon rubber.

Moreover, the treatment cap 151 comprises: puncturing needle passage holes 154a and 154b through which puncturing needles 158 are passed, which is formed substantially parallel to the longitudinal-axis direction of the treatment cap, and which have openings on the edge of the treatment cap body 152; puncturing needle insertion tubes 155a and 155b that communicate with the operator-side ends of the puncturing needle passage holes 154a and 154b, extend to the operator side of the endoscope 150, and has an airtight valve that is not shown; hard bar-like tissue retainer arms 156 that project from the edge of the treatment cap body 152 substantially parallel to the longitudinal-axis direction of the treatment cap; and a hard bar-like tissue retaining member 157 arched substantially in a semicircular form at the distal ends of the tissue retainer arms 156.

The endoscope 150 has a forceps passage channel 159 through which a cutter is passed, and a pair of clamp forceps passage channel 161 through which a pair of clamp forceps 160 is passed and whose distal part includes a forceps raiser 162 that deflects the projecting direction in which the pair of clamp forceps 160 is projected.

Figure 39:
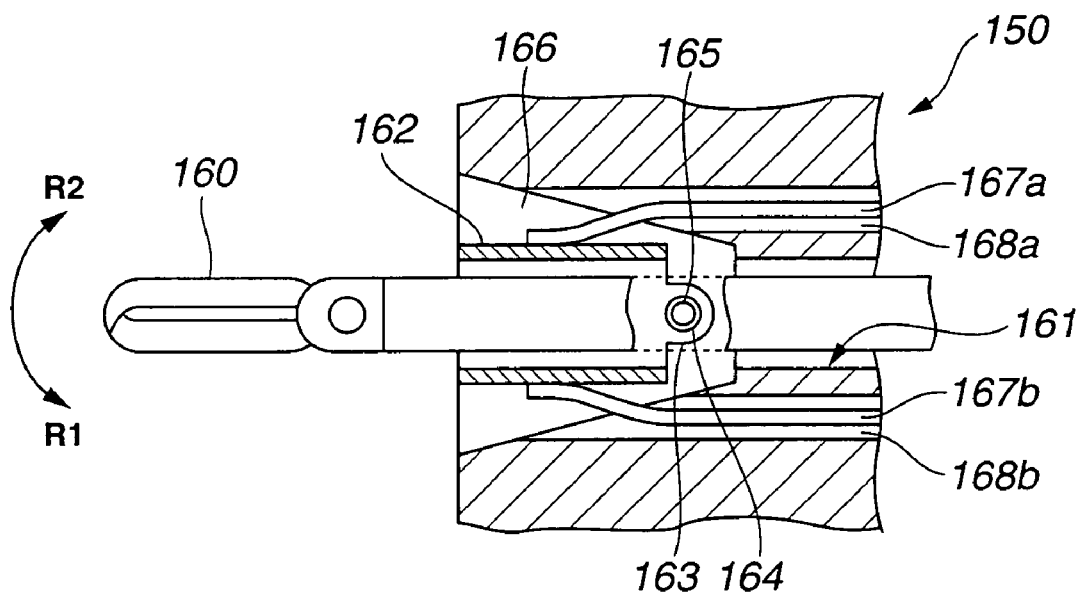
FIG. 39 is a sectional view showing a forceps raiser included in the therapeutic instruments insertion aid shown in FIG. 38.

The forceps raiser 162 is, as shown in FIG. 39, a cylindrical member whose inner diameter is substantially identical to or a little larger than that of the forceps passage channel 161. The forceps raiser 162 has a pair of collar members 163 that project from opposite positions at the operator-side end of the forceps raiser and are shaped like a substantially semi disk, and a hole 164 defined with the collar members 163. The forceps raiser 162 is accommodated in a forceps raiser storage 166 that is formed in the distal part of the forceps passage channel 161 and that opens wider upward and downward. A jut 164 disposed inside the forceps raiser storage 166 is freely slidably fitted in the hole 164. The hole 164 and jut 165 are disposed at a position substantially corresponding to a point on the axial center line shared by the forceps passage channel 161 and forceps raiser 162.

Forceps raiser operation wires 167a and 167b are vertically brazed to the external surface of the distal part of the forceps raiser 162. The forceps raiser operation wires 167a and 167b are passed through respective forceps raiser operation wire channels 168a and 168b and extended to an operating unit of the endoscope that is not shown. Moreover, the forceps raiser operation wires 167a and 167b are coupled to a forceps raiser lever that is not shown and thus freely moved in order to raise the pair of clamp forceps.

When the forceps raiser operation wire 167b is pulled with the pair of clamp forceps 160 passed through the forceps passage channel 161 lying through the endoscope 150, the pair of clamp forceps 160 can be projected in the direction of arrow R1 in FIG. 39 with respect to the endoscope 150. At this time, a metallic loop wire, which is projected, is passed through the cutter passage channel 159. A portion of the large intestine enclosed with the tissue retaining member 157, tissue retainer arms 156, and distal end of the treatment cap 151 is clamped.

In this state, the forceps raiser Wire 167b is thrust forward while the forceps raiser operation wire 167a is being pulled. This causes the forceps raiser 162 to raise the pair of clamp forceps 160 in the direction of arrow R2 in FIG. 39 with respect to the endoscope 150. Consequently, the large intestine clamped by the pair of clamp forceps 160 is lifted. In other words, the forceps raiser 162 fills the role of a lifting means or a lifting member for lifting a living-body tissue such as the large intestine. The pair of clamp forceps 160 and forceps raiser 162 constitute clamping and lifting means or a clamping and lifting member.

With the large intestine lifted, the puncturing needles 158 (see FIG. 38) are projected to pierce all the layers of the large intestine. Moreover, the large intestine is ligated with a ligature. When the ligation is completed, the metallic loop wire is tightened and a high-frequency current is fed to the metallic loop wire. Thus, the large intestine is resected.

Figure 40:
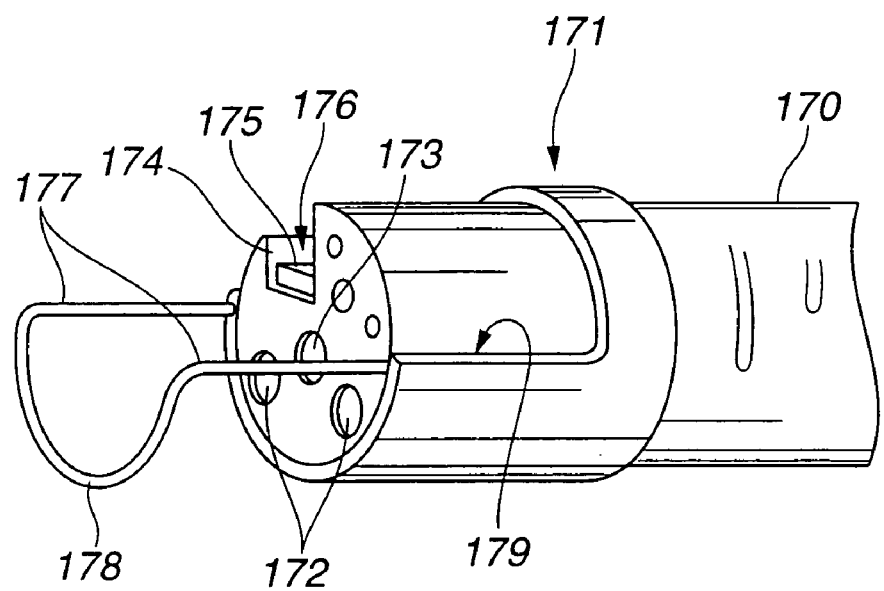
FIG. 40 is a perspective view showing the structure of another variant of the therapeutic instruments insertion aid shown in FIG. 36.

Moreover, as shown in FIG. 40, other variant of an endoscopic treatment system has a treatment cap 171 attached to an endoscope 170. The endoscope 170 has: puncturing needle passage channels 172; a cutter passage channel 173; a pair of clamp forceps passage channel 174; a forceps raiser 175 included in the distal part of the pair of clamp forceps passage channel 174; and a forceps raiser slit 176 that has substantially the same length as the forces raiser 175 and is formed in the external surface of the endoscope 170 below which the pair of clamp forceps passage channel 174 is formed.

Moreover, the treatment cap 171 has tissue retainer arms 177, and a tissue retainer 178 formed in a semicircular form at the distal ends of the tissue retainer arms 177. Moreover, the treatment cap 171 has a slit 176 whose length is substantially the same as the forceps raiser slit 176 with the treatment cap 171 attached to the endoscope 170.

Since the endoscope 170 has the forceps raiser slit 176, the range within which the forceps raiser 175 can raise the pair of clamp forceps becomes wider. Consequently, the large intestine or the like can be lifted higher.

When the treatment cap 151 or 171 having the foregoing structure is attached to the endoscope 150 or 170, an intended region can be ligated and resected easily.

Next, an endoscopic treatment system in accordance with a sixth embodiment of the present invention will be described in conjunction with FIG. 41 and FIG. 42.

A therapeutic instruments insertion aid 181 employed in the endoscopic treatment system in accordance with the sixth embodiment comprises: a distal treatment section 182 whose distal part includes a lateral hole 184, a slit 185, and puncturing needle passage channels and a cutter passage channel which are not shown; a therapeutic instruments insertion aid inserting section 183 that extends from the operator-side end of the distal treatment section 182 and that has an insertion unit slit 186 extending from the distal end of the therapeutic instruments insertion aid inserting section to the operator-side end thereof in the longitudinal-axis direction thereof; and puncturing needle passage tubes 187 and a cutter passage tube 188 whose distal parts are connected to the puncturing needle passage channels and cutter passage channel formed in the distal treatment section 182, which lie through the therapeutic instruments insertion aid inserting section 186, and which extend to the operator-side end of the therapeutic instruments insertion aid inserting section.

The therapeutic instruments insertion aid 181 having the foregoing structure is inserted into the large intestine with the distal treatment section 182 mounted on the outer surface of the endoscope 180 in advance. In order to insert the endoscope 180 to an intended region in the large intestine, the insertion unit of the endoscope 180 is led out of the therapeutic instruments insertion aid inserting section 183 through the insertion unit slit 186. The distal treatment section 182 is located on the operator side of the insertion unit of the endoscope 180 (see FIG. 41).

Thereafter, when the endoscope 180 is inserted into the intended region in the large intestine, the distal treatment section 182 is introduced into the large intestine while being moved along the insertion unit of the endoscope 180. At this time, the insertion unit of the endoscope 180 is put in the lumen of the therapeutic instruments insertion aid inserting section 183 through the insertion unit slit 186. After the insertion unit of the endoscope 180 is put in the lumen of the therapeutic instruments insertion aid inserting section 183, a tape member 189 is wound about the therapeutic instruments insertion aid inserting section 183 at a plurality of points at predetermined intervals for fear the insertion unit slit 186 may be left open. The insertion unit of the endoscope 180 is thus introduced into the large intestine (see FIG. 42).

The therapeutic instruments insertion aid 181 can be adapted to endoscopes whose insertion units have different lengths, by changing the point on the insertion unit of an endoscope, from which the insertion unit is put into the therapeutic instruments insertion aid inserting section 183 through the insertion unit slit 186.

Figure 43:
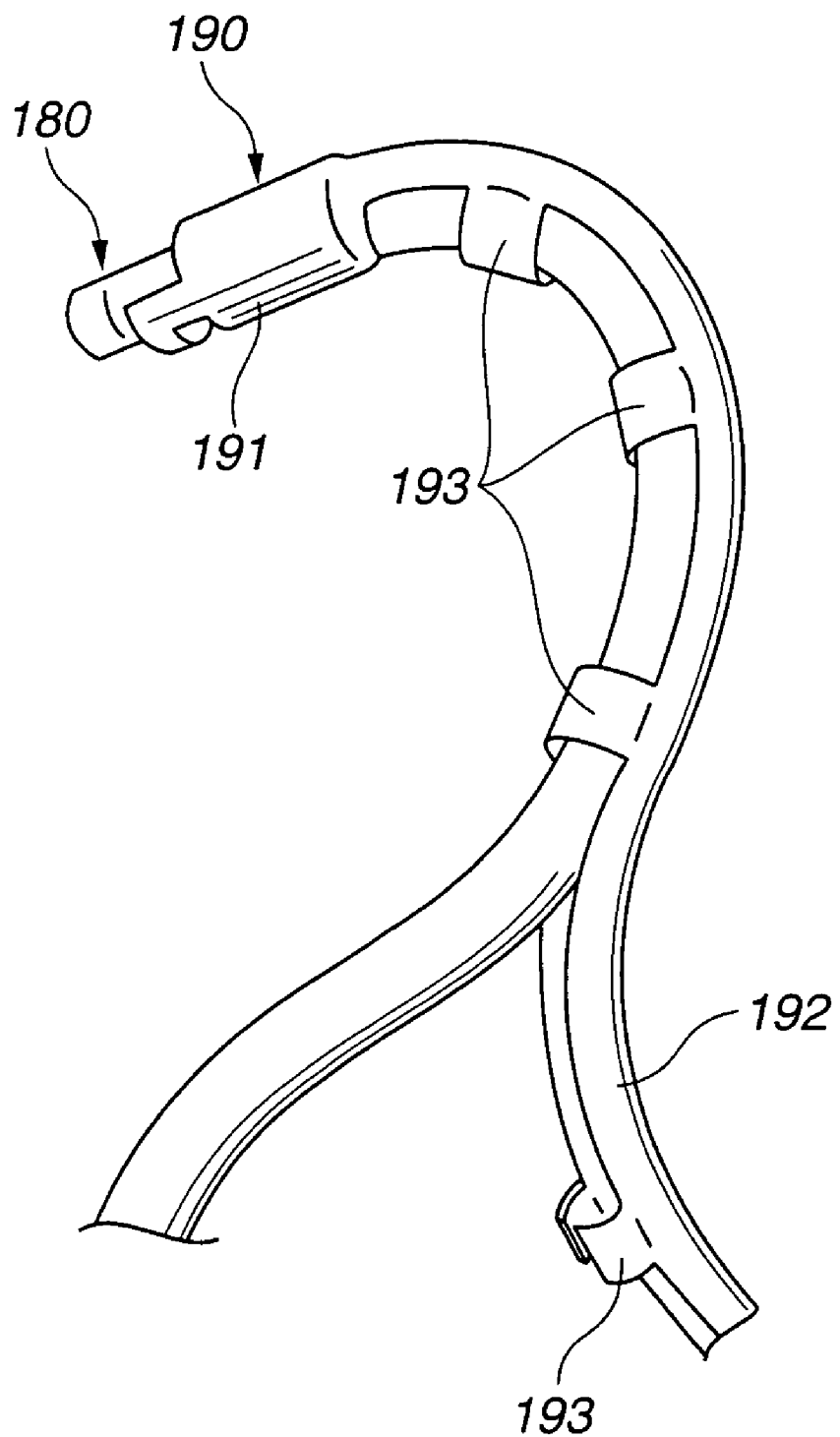
FIG. 43 is a perspective view showing the structure of a variant of the therapeutic instruments insertion aid shown in FIG. 41.

Next, a therapeutic instruments insertion aid 190 that is a variant of the therapeutic instruments insertion aid 181 included in the sixth embodiment will be described in conjunction with FIG. 43.

Figure 41:
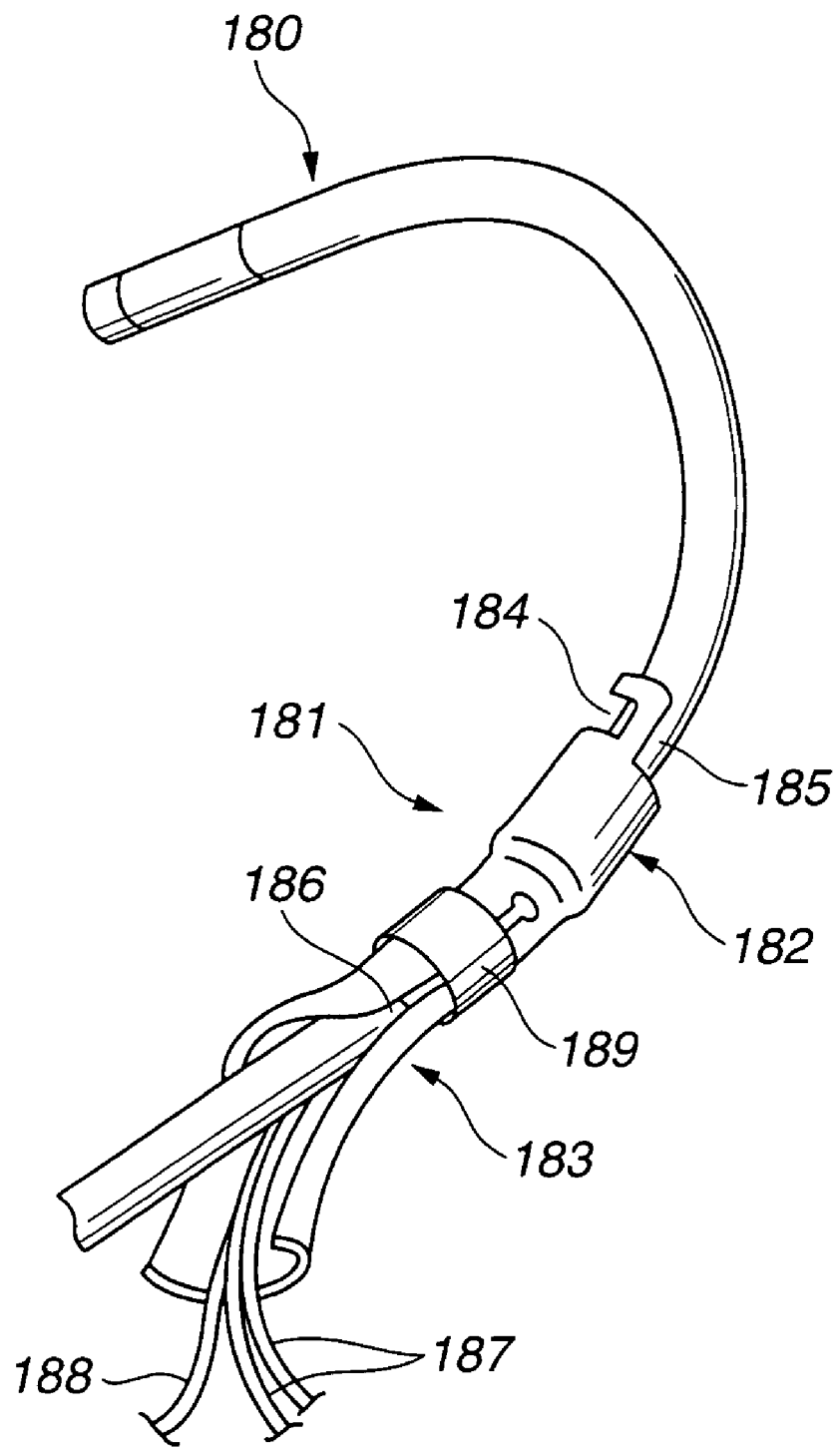
FIG. 41 is a perspective view showing the structure of a therapeutic instruments insertion aid employed in an endoscopic treatment system in accordance with a sixth embodiment of the present invention.
Figure 42:
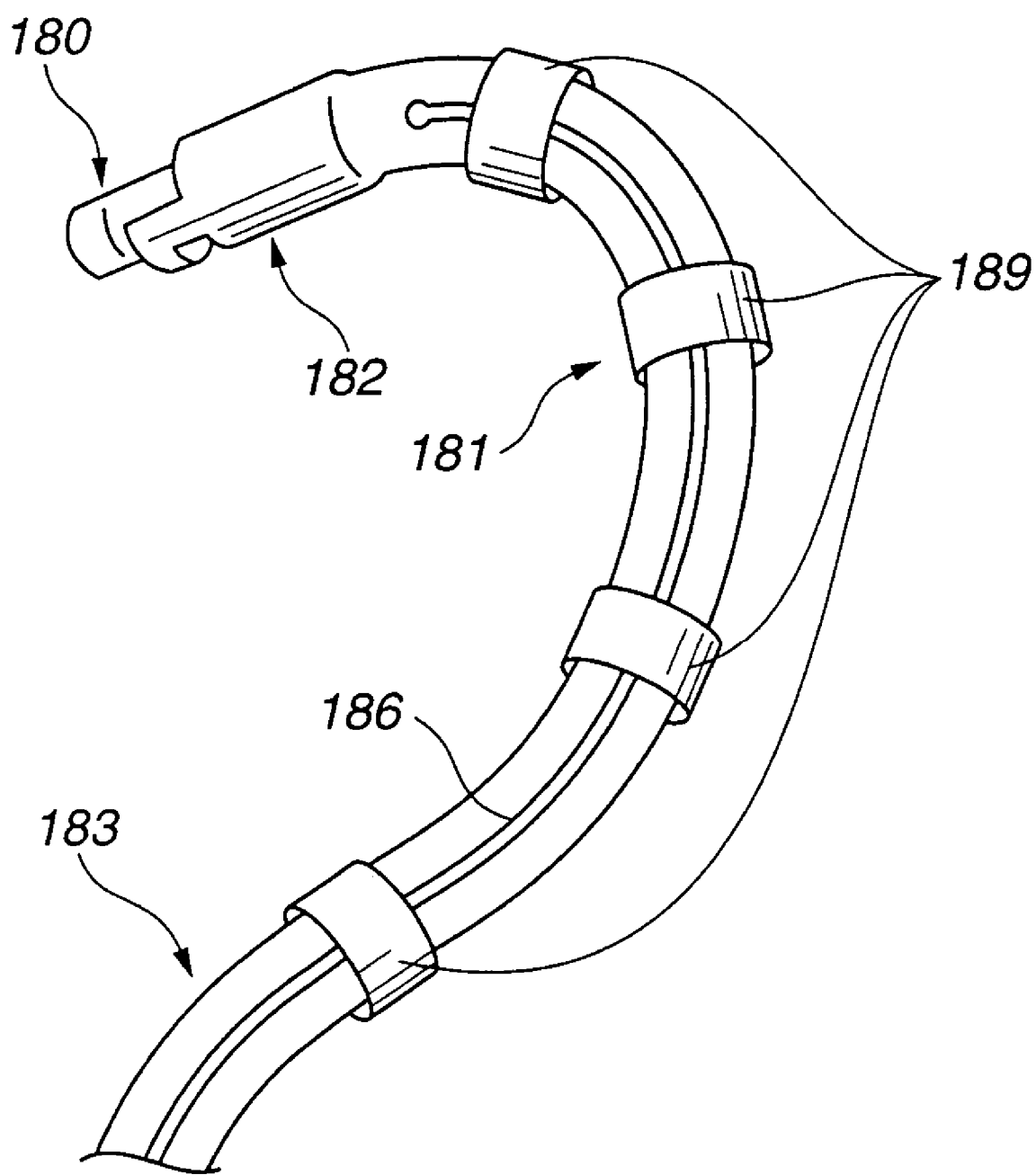
FIG. 42 is a perspective view showing an operation state of the therapeutic instruments insertion aid shown in FIG. 41.

The therapeutic instruments insertion aid 190 comprises: a distal treatment section 191 having the same capability as the distal treatment section 182 (see FIG. 41 and FIG. 42); and a therapeutic instruments insertion aid inserting section 192 having the same capability as the therapeutic instruments insertion aid inserting section 183 that has the insertion unit slit 186 (see FIG. 41 and FIG. 42). The therapeutic instruments insertion aid inserting section 192 has insertion unit locking members 193.

The plurality of insertion unit locking members 193 is formed at predetermined intervals as integral parts of the therapeutic instruments insertion aid inserting section 192. The insertion unit locking members 193 are shaped substantially in circular arc with partly notched on the insertion unit slit.

Specifically, when the distal treatment section 191 of the therapeutic instruments insertion aid 190 mounted on the outer surface of the endoscope 180 is inserted into the large intestine, the notches of the insertion unit locking members 193 are widened in order to put the insertion unit of the endoscope 180 into the therapeutic instruments insertion aid inserting section 192 through the widened notches.

Consequently, the endoscope insertion unit can be easily fitted into the therapeutic instruments insertion aid inserting section, and reliably run through or held in the therapeutic instruments insertion aid inserting section.

Next, various variants of an endoscopic treatment system in accordance with the present invention will be described in conjunction with FIG. 44 to FIG. 58.

Figure 44:
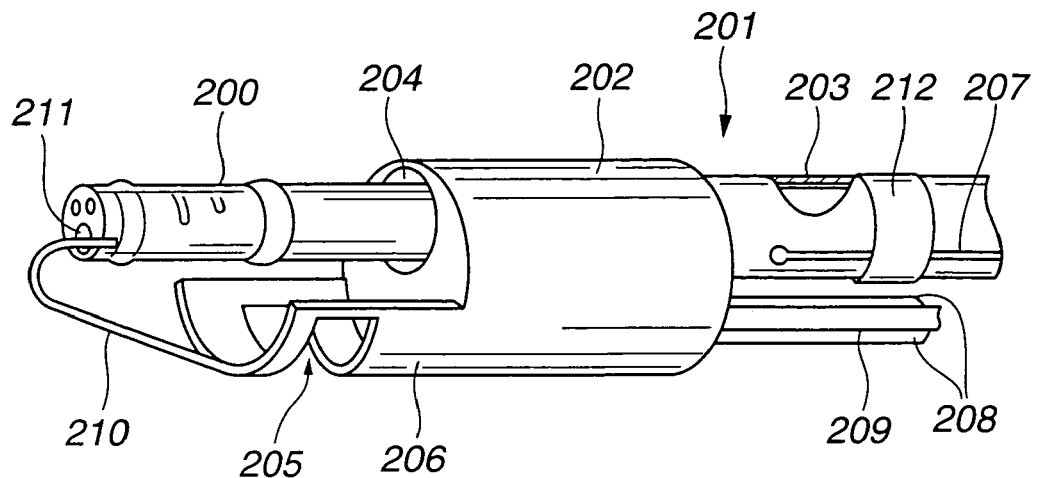
FIG. 44 is a perspective view showing the structure of a first another variant of the therapeutic instruments insertion aid employed in an endoscopic treatment system in accordance with the present invention.

FIG. 44 shows a first variant of a therapeutic instruments insertion aid employed in an endoscopic treatment system in accordance with the present invention, that is, a therapeutic instruments insertion aid 201 to be inserted into a deep region in the large intestine while being moved along an endoscope 200. The therapeutic instruments insertion aid 201 comprises: a hard substantially cylindrical distal treatment section 202 that has an endoscope passage channel 204 and a substantially plate-like tissue retainer sheet 206 which has a lateral hole 205 formed in the distal side thereof; puncturing needle passage channels and a cutter passage channel that are not shown and formed in the distal treatment section 202 in the longitudinal-axis direction of the distal treatment section; puncturing needle passage tubes 208 and a cutter passage tube 209 extending from the operator-side ends of the puncturing needle passage channels and cutter passage channel; a thin tube-like sheath 203 coupled to the operator-side end of the distal treatment section 202 and connected to the endoscope passage channel; and a guide strap 210 coupled to the distal end of the tissue retainer sheet 206 and extended to the operator-side of the endoscope through a treatment instrument passage channel 211 lying through the endoscope 200. Incidentally, the sheath 203 has a slit 207 extended in the longitudinal-axis direction thereof. Moreover, a locking tape 212 is wound about the sheath 203 at predetermined intervals.

The endoscope 200 is inserted in advance into the endoscope passage channel 204 formed in the distal treatment section 202 through the slit 207 of the sheath 203 of the therapeutic instruments insertion aid 201. Moreover, the guide strap 210 is inserted into the treatment instrument passage channel 211 lying through the endoscope 200. In other words, the distal insertion unit section of the endoscope 200 is jutted out of the endoscope passage channel 204 of the distal treatment section 202. The operator side of the insertion unit of the endoscope 200 is exposed to outside while coming out of the sheath 203 through the slit 207.

When the endoscope 200 is inserted into an intended region at the deep end of the large intestine, the guide strap 210 is pulled. Consequently, the distal treatment section 202 of the therapeutic instruments insertion aid 201 is led or inserted into the large intestine along the insertion unit of the endoscope 200.

As the therapeutic instruments insertion aid 201 is led or inserted into the large intestine, the insertion unit of the endoscope 200 is fitted or accommodated in the sheath 203 through the slit 207. Moreover, the locking tape 212 is wound about the sheath 203 at predetermined intervals.

After the therapeutic instruments insertion aid 201 is led or inserted into the intended region in the large intestine, the endoscope 200 may be replaced with a side-vision endoscope.

As mentioned above, the therapeutic instruments insertion aid 201 is led or inserted from the distal part thereof along the endoscope. This leads to the improved maneuverability in inserting the therapeutic instruments insertion aid 201. Moreover, the guide strap 210 is pulled in order to insert the therapeutic instruments insertion aid 201. Therefore, the sheath 203 can be made easy to bend and thin. Eventually, the sheath 203 of the therapeutic instruments insertion aid 201 can be formed to have a small diameter.

Figure 45:
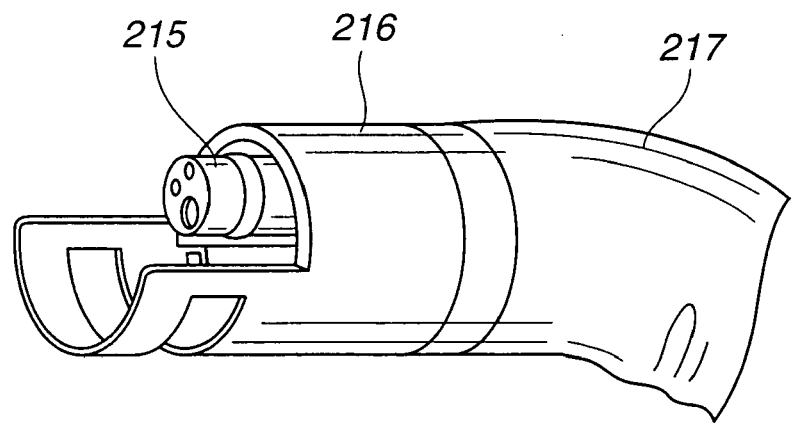
FIG. 45 is a perspective view showing the structure of a second another variant of the therapeutic instruments insertion aid employed in an endoscopic treatment system in accordance with the present invention.

Like a second variant of a therapeutic instruments insertion aid employed in an endoscopic treatment system in accordance with the present invention which is shown in FIG. 45, a therapeutic instruments insertion aid 216 mounted on the outer surface of an endoscope 215 may have a bending section 217 included in a distal part thereof so that the bending section 217 can be bent together with the bending section of the endoscope 215 that is not shown. This results in the improved maneuverability in inserting the therapeutic instruments insertion aid 216.

Figure 46:
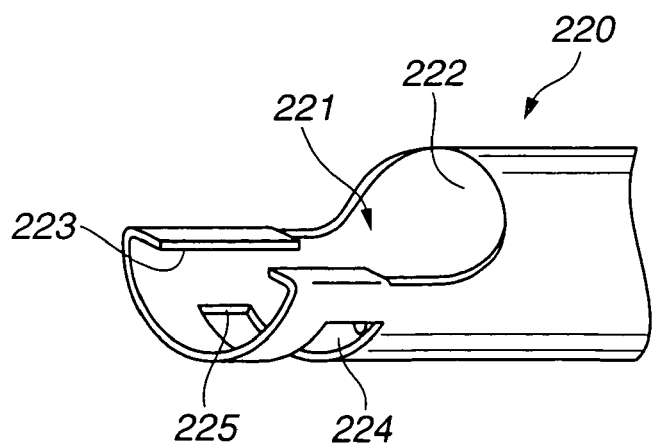
FIG. 46 is a perspective view showing the structure of another variant of the distal part of the therapeutic instruments insertion aid employed in an endoscopic treatment system in accordance with the present invention.
Figure 47:
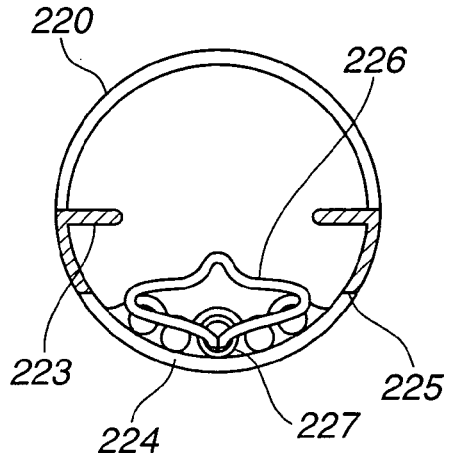
FIG. 47 is a sectional view showing a lateral hole bored in the therapeutic instruments insertion aid shown in FIG. 46.
Figure 48:
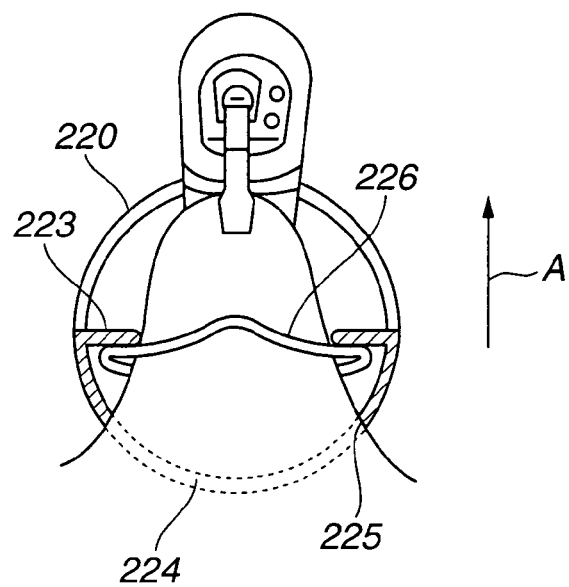
FIG. 48 is a sectional view showing a state of an intended region lifted with the therapeutic instruments insertion aid shown in FIG. 46.

FIG. 46, FIG. 47, and FIG. 48 show variants of the distal structure of a therapeutic instruments insertion aid employed in an endoscopic treatment system in accordance with the present invention.

As shown in FIG. 46, a therapeutic instruments insertion aid 220 has an endoscope passage channel 222 and is shaped substantially like a cylinder. The therapeutic instruments insertion aid 220 has a slit 221 formed by cutting off the substantially upper half of the distal part of the therapeutic instruments insertion aid 220 which has an arc section, and a lateral hole 224 formed in the substantially lower half of the distal part thereof which has an arc section. Substantially plate-like projection members 223, projecting towards the inside of the therapeutic instruments insertion aid 220, are extended from both edge of the arc which forms the lateral hole 224 and is formed at the substantially lower half of the distal end thereof. The projection members 223 will be substantially parallel to the lateral sides 225 of the lateral hole 224.

The therapeutic instruments insertion aid 220 having the foregoing structure has, as shown in FIG. 47, a metallic loop wire 226 jutted out of a cutter passage channel 227 and extended along the lateral sides 225 of the lateral hole 224.

In this state, a pair of clamp forceps passed through an endoscope is used to clamp and lift an intended region in the large intestine through the lateral hole 224 and metallic loop wire 226. Consequently, the intended region that is clamped and lifted is, as shown in FIG. 48, raised in the direction of arrow A in FIG. 48 through the metallic loop wire 226 and lateral hole 224. The metallic loop wire 226 is blocked by the projection members 223 and will not be raised any more. Thus, the metallic loop wire can be reliably positioned near the skirt of the intended region that is clamped and lifted. By pulling the metallic loop wire 226, the intended region can be constricted successfully. At the same time, if a high-frequency current flows into the metallic loop wire 226, the large intestine can be resected.

Figure 49:
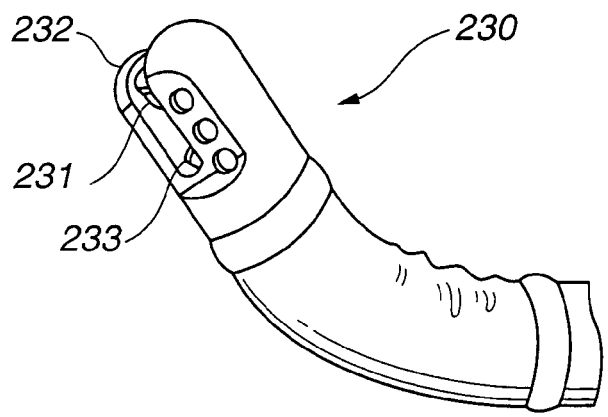
FIG. 49 is an explanatory diagram showing the distal part of an insertion unit of a side-vision endoscope employed in an endoscopic treatment system in accordance with the present invention.
Figure 50:
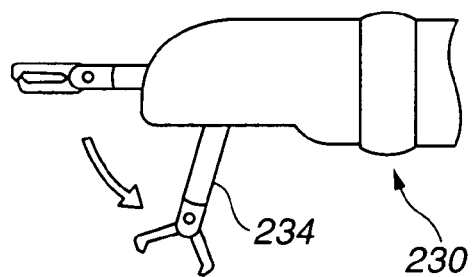
FIG. 50 is an explanatory diagram showing raising of a pair of clamp forceps lying through the side-vision endoscope shown in FIG. 49.

FIG. 49 and FIG. 50 show examples of a case where a side-vision endoscope is employed in an endoscopic treatment system in accordance with the present invention.

The distal part of an insertion unit of a side-vision endoscope 230 employed in an endoscopic treatment system in accordance with the present invention has a slit 232 extended substantially linearly from an opening of a treatment instrument passage channel 233. A forceps raiser 231 is disposed in the slit 232.

In the side-vision endoscope 230, as shown in FIG. 50, the hard distal section is long. Even a pair of clamp forceps 234 that cannot be placed on a forceps raiser in a usual side-vision endoscope can be jutted out to the distal section of the endoscope with the forceps raiser 231 being laid down. When the forceps raiser 231 is raised, the pair of clamp forceps 234 can be projected in any direction.

Next, a variant of a therapeutic instruments insertion aid employed in an endoscopic treatment system in accordance with the present invention will be described in conjunction with FIG. 51 and FIG. 52.

Figure 51:
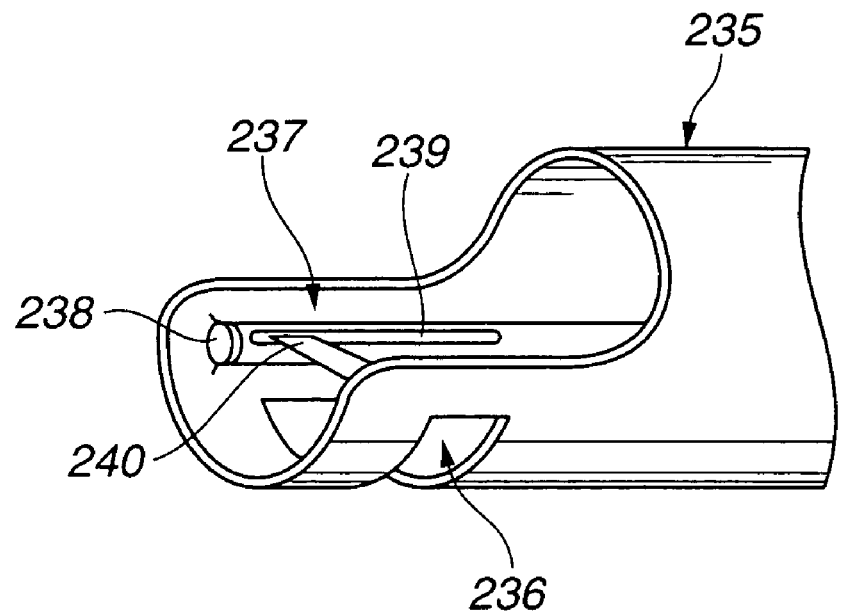
FIG. 51 is a perspective view showing the structure of a cutter, that is, another variant of the therapeutic instruments insertion aid employed in an endoscopic treatment system in accordance with the present invention.
Figure 52:
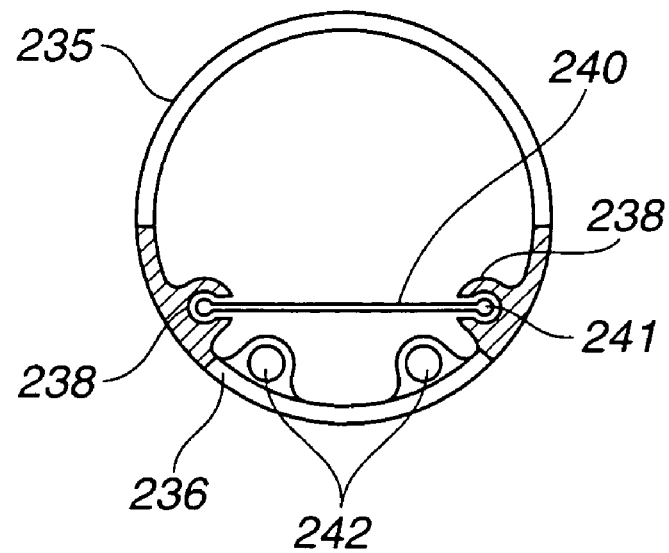
FIG. 52 is a sectional view showing the structure of the cutter shown in FIG. 51.

As shown in FIG. 51, a therapeutic instruments insertion aid 235 of a variant has two cutter channels 238, which lie near a slit 237 rather than near the lateral sides of a lateral hole 236 in the distal lumen of the therapeutic instruments insertion aid and which extend from the distal end of the therapeutic instruments insertion aid to the operator-side end thereof, located at opposite positions. The cutter channels 238 each has a cutter slit 239 whose length is equivalent at least to the length from the distal side of the lateral hole 236 to the proximal side thereof. The cutter channels 238 have a resection blade 240, which is shaped substantially like a plate and which has an edge at least either on the distal side or proximal side thereof, and is laid between the cutter slits 239. In each of the cutter channels 238, as shown in FIG. 52, an operation wire 241 whose distal end is coupled to the resection blade 240 and whose proximal-side end is extended to the operator end of the therapeutic instruments insertion aid 235 is disposed so that the operation wire 241 can be advanced or withdrawn through the cutter channel 238 by means of a handle that is not shown.

When the operation wire 241 is thrust forward, the resection blade 240 is located at the distal end of the therapeutic instruments insertion aid 235 beyond the lateral hole 236. In this state, the large intestine is lifted through the lateral hole 236. The lifted large intestine is pierced and ligated using puncturing needles jutted out of puncturing needle channels 242. Thereafter, the operation wire 241 is pulled in order to resect the large intestine using the resection blade 240. At this time, a high-frequency current may be conducted to the resection blade 240.

Figure 53:
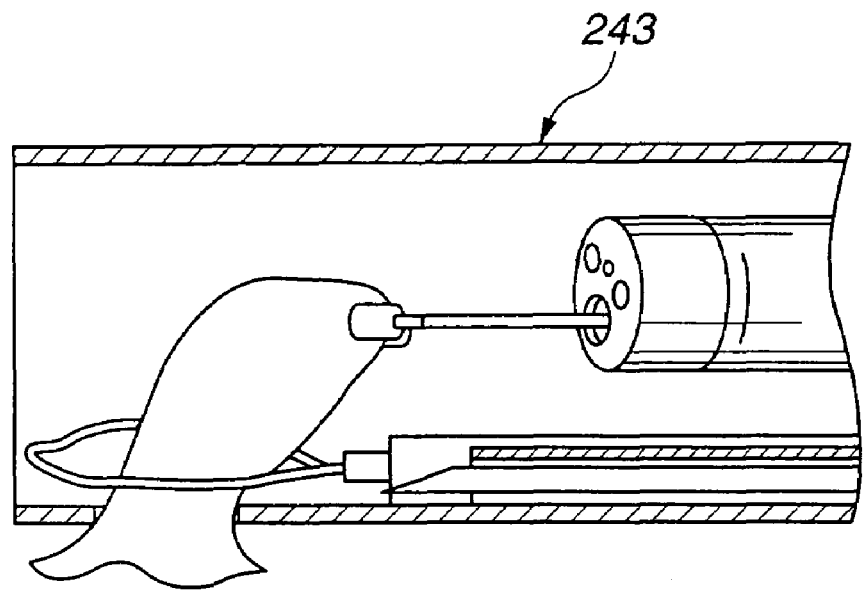
FIG. 53 is a sectional view showing an applied example of the therapeutic instruments insertion aid shown in FIG. 51.

In an applied case shown in FIG. 53, a therapeutic instruments insertion aid 243 is devoid of the slit 237 shown in FIG. 51. Consequently, the tissues of the large intestine can be clamped and lifted or pierced and ligated within the therapeutic instruments insertion aid 243.

Next, other variant of a therapeutic instruments insertion aid employed in an endoscopic treatment system in accordance with the present invention will be described in conjunction with FIG. 54, FIG. 55, and FIG. 56.

Figure 54:
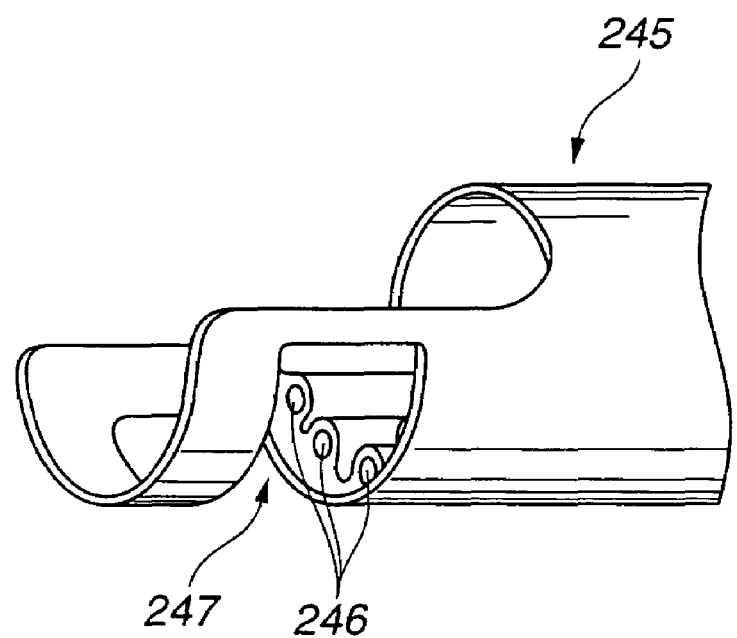
FIG. 54 is a perspective view showing the structure of further another variant of the therapeutic instruments insertion aid employed in an endoscopic treatment system in accordance with the present invention.
Figure 55:
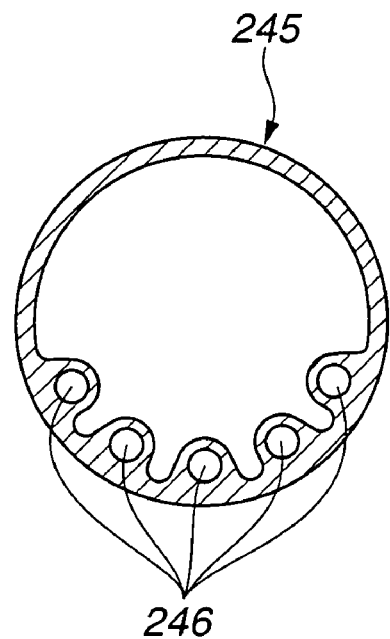
FIG. 55 is a sectional view showing the structure of the therapeutic instruments insertion aid shown in FIG. 54.

A therapeutic instruments insertion aid 245 of a variant includes two or more puncturing needle passage channels 246, for example, as shown in FIG. 54 and FIG. 55, five puncturing needle passage channels 246. The distal ends of the puncturing needle passage channels 246 are located in front of a lateral hole 247. Incidentally, the therapeutic instruments insertion aid 245 has, in addition to the puncturing needle passage channels 246, an endoscope passage channel through which an endoscope, into which a pair of clamp forceps that is not shown can be inserted, is passed, and a cutter passage channel through which a cutter is passed.

Figure 56:
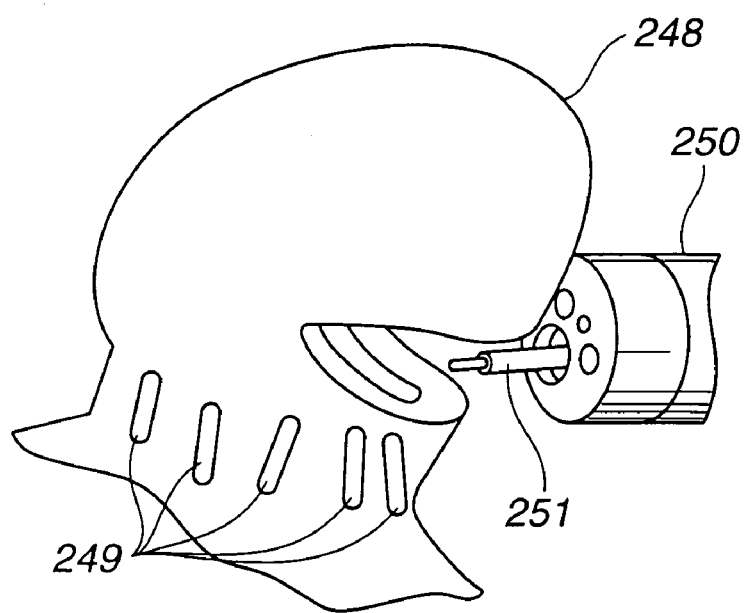
FIG. 56 is an explanatory diagram concerning ligation and resection of an intended region performed using the therapeutic instruments insertion aid shown in FIG. 54.

Using the therapeutic instruments insertion aid 245, puncturing needles are, as shown in FIG. 56, pierced into an intended region, for example, in the large intestine, and ligatures 249 are pierced into all the layers of the large intestine. Owing to the plurality of ligatures 249, the intended region in the large intestine 248 having all the layers thereof ligated substantially in the form of a polyp has all the layers thereof resected by means of an electrocautery 251 passed through the endoscope 250.

Consequently, the therapeutic instruments insertion aid 245 permits concurrent use of a plurality of ligatures for punctuation and ligation. Ligation can-be achieved concisely.

Figure 57:
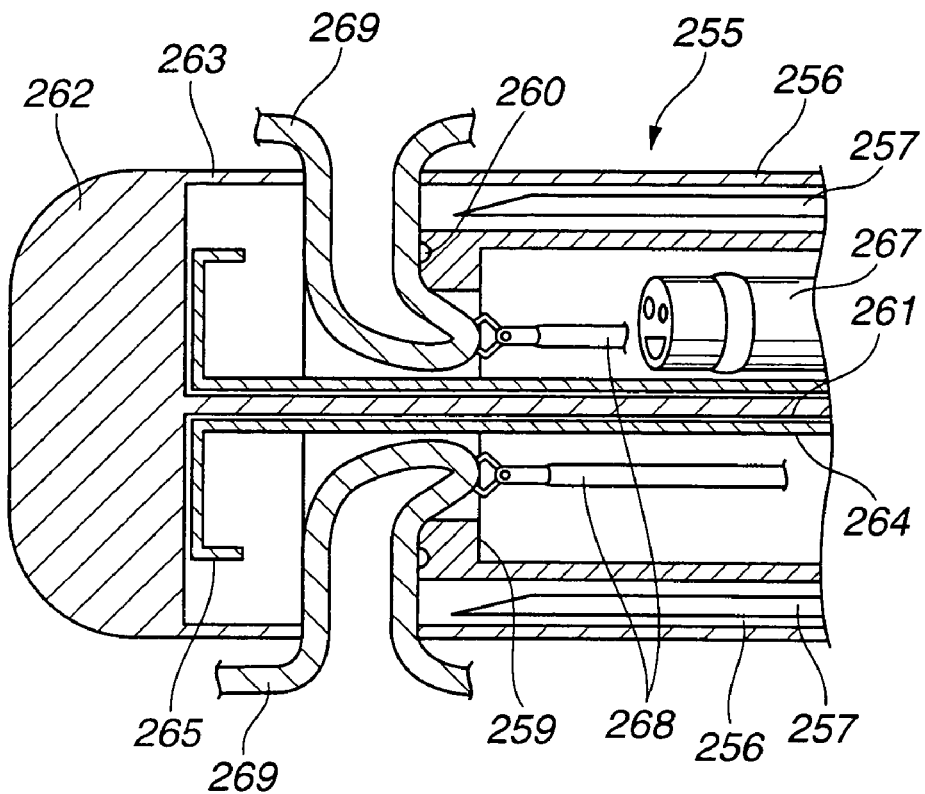
FIG. 57 is a sectional view showing the structure of another applied example of the therapeutic instruments insertion aid employed in an endoscopic-treatment system in accordance with the present invention.
Figure 58:
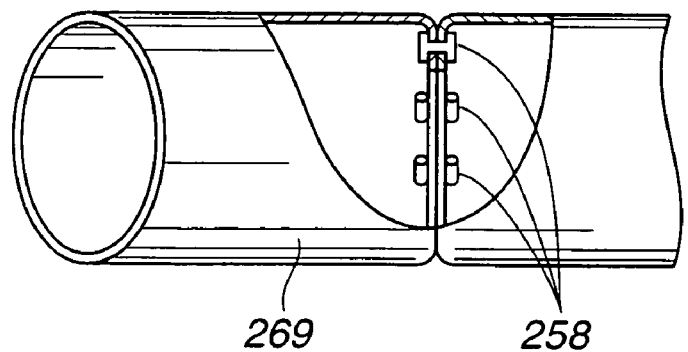
FIG. 58 is an explanatory diagram showing a state of the large intestine ligated and resected using the therapeutic instruments insertion aid shown in FIG. 57.

Next, other example to which a therapeutic instruments insertion aid employed in an endoscopic treatment system in accordance with the present invention is adapted will be described in conjunction with FIG. 57 and FIG. 58.

A therapeutic instruments insertion aid 255 is other example to which a therapeutic instruments insertion aid employed in an endoscopic treatment system in accordance with the present invention is applied. The therapeutic instruments insertion aid 255 has, as shown in FIG. 57, a plurality of puncturing needle passage channels 256 formed on the full circumference at regular intervals in the lumen of the therapeutic instruments insertion aid 255.

Puncturing needles 257 are run through the respective puncturing needle passage channels 256. A ligature 258 (see FIG. 58) is disposed in the lumen of each puncturing needle 257, though it is not shown. The ligature 258 is, as shown in FIG. 58, shaped substantially like letter H and composed of a ligation shaft and locking members formed at both ends of the ligation shaft. During ligation, all the layers of the large intestine 269 are sandwiched between the locking members in order to lock the large intestine (see FIG. 15 showing the ligation unit 64 employed in the second embodiment).

A projection 259 is formed on the full circumference at the distal end of the therapeutic instruments insertion aid 255 inside the therapeutic instruments insertion aid 255 beyond the puncturing needle passage channels 256. A groove-like resection blade receptor 260 is formed on the full circumference in the distal end surface of the projection 259.

A distal hood 262 is disposed at the distal end of a distal hood operation shaft 261 coaxial to the center axis of the therapeutic instruments insertion aid 255. A rim-like lower edge 263 is provided on the outer surface of the operator-side end of the distal hood. The lower edge 263 is substantially abutted on the distal outer surface of the therapeutic instruments insertion aid 255. A resecting member 265 having a resection blade extended like a rim from the outer surface thereof and being shaped substantially like a disk is arranged at the distal end of a resection blade operation shaft 264 that includes the distal hood operating shaft 261. The blade of the resecting member 265 abuts on the groove of the resection blade receptor 260.

When the distal hood operation shaft 261 and resection blade operation shaft 264 are projected, a space is created among the distal end of the therapeutic instruments insertion aid 255 and the lower edge 263 and resecting member 265. Through the space, all the layers of the large intestine 269 are led into the therapeutic instruments insertion aid 255 using a pair of clamp forceps 268 under observation through an endoscope 267. With the large intestine led in, the distal hood operation shaft 261 is pulled. Consequently, the large intestine is sandwiched between the lower edge 263 and the outer surface of the therapeutic instruments insertion aid 255, and thus immobilized.

Thereafter, all the layers of the large intestine 269 are pierced with the puncturing needles 257. The ligatures 258 are thrust forward in order to ligate all the layers of the large intestine 269. After the completion of the ligation, the resection blade operation shaft 264 is pulled such that the resection blade of the resecting member 265 will be abutted on the resection blade receptor 260. Consequently, all the layers of the large intestine 269 are resected over the full circumference at a time. Herein, the puncturing needles 257, ligatures 258, and resecting member 265 constitute puncturing and ligating means.

Since the puncturing and ligating means and resecting means are formed over the full circumference, a portion of the large intestine can be resected over the full circumference at a time.

According to the present invention, it is apparent that a wide range of different embodiments can be formed based on the invention without a departure from the spirit or scope of the invention. The present invention will be limited to appended claims but not restricted to any specific embodiments.

What is claimed is:

1. An endoscopic treatment system comprising:
  a first insertion instrument;
  a second insertion instrument into which the first insertion instrument is inserted;
  an observation device included in either the first insertion instrument or the second insertion instrument and used to observe a living-body tissue;
  a clamping and lifting member that is included in the first insertion instrument and that has a clamping member which clamps the living-body tissue that is an object of treatment, and a lifting member which lifts the living-body tissue though bending;

a tissue retainer member that is included in the second insertion instrument and that controls the lifting of a peripheral tissue of the living-body tissue clamped and lifted by the clamping and lifting member included in the first insertion instrument;

a ligating member that ligates the living-body tissue; and a resecting member that resects the living-body tissue at a position between a region ligated by the ligating member and a region clamped by the clamping and lifting member;

wherein the inserting sections of the first and second insertion instruments which are inserted into a living-body duct are formed with flexible members;

the clamping member is a pair of clamp forceps that is inserted in a treatment instrument passage channel lying through the first insertion instrument;

a lateral hole is formed in the lateral side on the outer periphery of the second insertion instrument; and a slit is formed in the lateral side on the outer periphery of the second insertion instrument opposing the lateral hole.

2. The endoscopic treatment system according to claim 1, wherein the first insertion instrument is an endoscope having the observation device.

3. The endoscopic treatment system according to claim 2, wherein the endoscope is of a direct-vision type and includes a forceps raising member which swings the distal end of a treatment instrument, which is passed through the treatment instrument passage channel.

4. The endoscopic treatment system according to claim 2, wherein the endoscope is a direct-vision endoscope having two or more bending sections, which can be bent independently by an operator.

5. The endoscopic treatment system according to claim 1, wherein the endoscope is of a side-vision or oblique-vision type.

6. The endoscopic treatment system according to claim 5, wherein the upper side of an image displayed on a monitor included in the side-vision or oblique-vision endoscope faces the distal side of the insertion unit of the endoscope.

7. The endoscopic treatment system according to claim 5, wherein the tissue retaining member includes: a receiving member that is located in more distal end of the second insertion instrument than the ligating member is, and that is formed with a substantially bar-like or plate-like member; and arm members that are connected to the receiving member.

8. The endoscopic treatment system according to claim 7, wherein the receiving member is movable in a direction substantially parallel to the direction of the axis of movement of the ligating member.

9. The endoscopic treatment system according to claim 1, wherein the ligating member is a stapler comprising: a plurality of elastic staples located on the operator side of the tissue retaining member; a thrusting member for thrusting the elastic staples; an operating member coupled to the operator-side end of the thrusting member and extended from the distal end of the therapeutic instruments insertion aid to the operator-side end thereof; and a receiving member which is formed on the distal side of the lateral hole, on which the thrust elastic staples are abutted, and which bends the feet of the elastic staples.

10. The endoscopic treatment system according to claim 9, wherein the resecting member is a cutter.

11. The endoscopic treatment system according to claim 10, wherein, the resecting member is interposed at least between a lesion to be resected and the ligating member, and the resecting member is located at a position where a living-body tissue, which is 1 mm or more wide, lies between a resecting plane on which the resecting member moves and a lesion and a region to be sutured.

12. The endoscopic treatment system according to claim 11, wherein the ligating member and resecting member are formed over the full circumference around the internal surface of the second insertion instrument.

13. The endoscopic treatment system according to claim 9, wherein the resecting member is a snare extending from the operator-side end of the second insertion instrument to the distal end thereof and having a loop-like metallic wire at the distal end thereof.

14. The endoscopic treatment system according to claim 13, wherein a snare locking member that locks the loop of the snare such that the loop can be freely unlocked is formed around the lateral hole in the distal part of the second insertion instrument.

15. The endoscopic treatment system according to claim 13, wherein a substantially plate-like floating suppressing member for suppressing movements of the loop of the snare is included in the distal part of the second insertion instrument.

16. The endoscopic treatment system according to claim 1, wherein the ligating member includes a substantially strap-like coupling member and securing members which are formed at both ends of the coupling member and whose diameter is larger than that of the coupling member, and the securing member is held in the lumen of a puncturing needle.

17. The endoscopic treatment system according to claim 16, wherein the puncturing member is a puncturing needle, and the tip of the puncturing needle moves from the operator-side end of the second insertion instrument to the distal end thereof.

18. The endoscopic treatment system according to claim 17, wherein two or more puncturing needles are included as the puncturing needle.

19. The endoscopic treatment system according to claim 1, further comprising a securing member that is freely attachable or detachable and fixed to at least either of the first insertion instrument and the second insertion instrument so as to lock each other.

20. An endoscopic treatment method comprising the steps of:

inserting an endoscope into an intended region in a living body's duct;

inserting a first insertion instrument mounted on the outer surface of the endoscope;

exchanging the endoscope for a second insertion instrument;

clamping a living-body tissue positioned in a lateral hole formed in an outer periphery of an insertion part of the first insertion instrument;

lifting the clamped living-body tissue so as to draw it into the lateral hole using the second insertion instrument;

ligating the lifted living-body tissue using the ligating member;

resecting the ligated living-body tissue at a position between the ligated region of the living-body and the clamped region thereof; and removing and collecting the resected living-body tissue together with the second insertion instrument.

21. An endoscopic treatment system comprising:
a first insertion instrument;
a second insertion instrument into which the first insertion instrument is inserted;
an observation device included in either the first insertion instrument or the second insertion instrument and used to observe a living-body tissue;
a clamping and lifting member that is included in the first insertion instrument and that has a clamping member which clamps the living-body tissue that is an object of treatment, and a lifting member which lifts the living-body tissue though bending;
a tissue retainer member that is included in the second insertion instrument and that controls the lifting of a peripheral tissue of the living-body tissue clamped and lifted by the clamping and lifting member included in the first insertion instrument;
a ligating member that ligates the living-body tissue; and
a resecting member that resects the living-body tissue at a position between a region ligated by the ligating member and a region clamped by the clamping and lifting member;
wherein the second insertion instrument includes a bending mechanism.

22. The endoscopic treatment system according to claim 21, wherein the second insertion instrument is an endoscope.

23. The endoscopic treatment system according to claim 22, wherein the endoscope is of a side-vision or oblique-vision type.

24. The endoscopic treatment system according to claim 22, wherein the endoscope is of a direct-vision type.

25. An endoscopic treatment system comprising:
a first insertion instrument;
a second insertion instrument into which the first insertion instrument is inserted;
an observation device included in either the first insertion instrument or the second insertion instrument and used to observe a living-body tissue;
a clamping and lifting member that is included in the first insertion instrument and that has a clamping member which clamps the living-body tissue that is an object of treatment, and a lifting member which lifts the living-body tissue through bending;
a tissue retainer member that is included in the second insertion instrument and that controls the lifting of a peripheral tissue of the living-body tissue clamped and lifted by the clamping and lifting member included in the first insertion instrument;
a ligating member that ligates the living-body tissue; and
a resecting member that resects the living-body tissue at a position between a region ligated by the ligating member and a region clamped by the clamping and lifting member;
wherein the second insertion instrument has puncturing needle and ligature passage channels through which respective puncturing needles and ligatures are passed;
a receiving member located in more distant end of the second insertion instrument than the puncturing needle and ligature passage channels are, and formed with a bar-like or plate-like member; and
arm members that link the distal end of the second insertion instrument and the receiving member.

26. The endoscopic treatment system according to claim 25, wherein the tissue retainer member is detachable from the second insertion instrument.

27. A treatment device, comprising:
an insertion portion having a lumen into which an insertion instrument including a clamping member is inserted;
a tissue retainer member which is provided in the insertion portion and which controls the lifting of a peripheral tissue of the tissue clamped and lifted by the insertion instrument;
a slit provided in an area opposite to the tissue retainer member with the center of the lumen therebetween, the slit permitting the distal end of the insertion instrument to be bent away from the center of the lumen in order to lift the tissue;
a ligating member which ligates the tissue; and
a resecting member which resects the tissue at a position between a region ligated by the ligating member and a region clamped by the insertion instrument.

* * * * *